(12) United States Patent
Allen et al.

(10) Patent No.: US 6,338,856 B1
(45) Date of Patent: Jan. 15, 2002

(54) SEAWEED SUPPLEMENT DIET FOR ENHANCING IMMUNE RESPONSE IN MAMMALS AND POULTRY

(75) Inventors: Vivien Gore Allen, Lubbock; Kevin R. Pond, Wolfforth, both of TX (US)

(73) Assignee: Texas Tech University, Lubbock, TX (US)

( * ) Notice: Subject to any disclaimer, the term of this patent is extended or adjusted under 35 U.S.C. 154(b) by 0 days.

(21) Appl. No.: 09/469,176

(22) Filed: Dec. 21, 1999

Related U.S. Application Data

(63) Continuation-in-part of application No. 09/032,104, filed on Feb. 27, 1998.

(51) Int. Cl.[7] .................................................. A23K 1/16
(52) U.S. Cl. ................... 424/442; 424/195.17; 514/885
(58) Field of Search ................... 424/439, 442, 424/575, 195.17; 514/885; 426/2, 53, 635

(56) References Cited

U.S. PATENT DOCUMENTS 5,229,118 A * 7/1993 Campbell ................. 424/195.1

FOREIGN PATENT DOCUMENTS

| BE | 626884 | * | 1/1963 |
| JP | 5440176 | * | 3/1979 |

OTHER PUBLICATIONS

Effects of dietary *Ascophyllum nodosum* on blood parameters of rats and pigs Jones. et al Bot. Mar. (1979), 22(6), 393–4, 1979.*

Efficiency of fucans in protecting porcine endothelial cells against complement activation and lysis by human serum Charreau, etal Transplant. Proc. (199 ), 29(1/2), 889–890, 1997.*

Iodine requirement of weaning piglets of southern Belorussian SSR Lemesh, V. F.; Prokoshin, A. A. USSR Vestsi Akad. Navuk Belarus. SSR, Ser. Sel'skagaspad. Navuk (1970), (2), pp. 105–9, 1970.*

Kim, C. S., et al., The Effect of Dietary Sargassum–Natans and Ascophyllum–Nodosum on Salmonella Gallinarum Infection in Chicks, BIOSIS (AN 1969:8848).

Herskoviz, R., et al., Differential effects of Polysulfated polysaccharide on experimental encephalomyelitis, proliferation of autoimmune T cells, and inhibition of heparanase activity, BIOSIS (AN 1996:22174).

Matsuzaki, S., et al., Application of seaweeds to human nutrition and medicine CA (AN97:4974).

Nishizawa, K., Seaweed as food for controlling diseases in elderly patients, CAPLUS (AN 1998:590009).

Kim, C. S., The Effects of Dietary Sargassum–Natans and Ascophyllum–Nodosum on Salmonella–Gallinarum Infection in Chicks, BIOSIS (AN 1973:82740).

(List continued on next page.)

*Primary Examiner*—Neil S. Levy

(57) ABSTRACT

Seaweed supplement is included in diet of mammals and poultry to enhance immune response. In one embodiment, pasture forage is treated with seaweed supplement. When cattle or lambs are grazed on seaweed supplement treated endophyte-infected forage, immune function is preserved or depressed immune function is reversed. The enhanced immune function continues to the feedlot finishing phase even though no seaweed supplement is fed in that phase. In an independently inventive embodiment, seaweed supplement is administered to pigs exposed to PRRS disease to impart resistance to said disease and improve performance. In still another independently inventive embodiment, seaweed supplement is administered to lactating mares prior to weaning to mitigate the stress of weaning.

8 Claims, 21 Drawing Sheets

OTHER PUBLICATIONS

Charreau, B., et al., Efficiency of fucans in protecting porcine endothelial cells against complement activation and lysis by human serum, BIOSIS (AN 1997:190627).

Blondin, C., et al., Relationships between chemical characteristics and anticomplementary activity of fucans, BIOSYS (AN 1996:188236).

Ren, D., et al., Study on Antihypertensive and Antihyperlipidemic Effects of Marine Algae, BIOSIS (AN 1994:487915).

Klinger, M. M., et al., Anti–HIV Activity of Sulfated Polysaccharides from the Brown Seaweed *Ascophyllum nodosum*, DRUGU M (AN 91–25081).

Blunden, G., et al., Medicinal and Pharmaceutical Uses of Algae, DRUGU TMPS (AN 87–01915).

Brochure titled Field Trial Summaries, Impact of Acadian Seaplants Seaweed Extract on Agricultural Crops, Acadian Seaplants Limited, Nova Scotia, Canada 2000.

Product and Technical Information, *Ascophylluns nodosum* Kelp Meal and Flour, Acadian Seaplants Limited, Nova Scotia, Canada (Jan. 10, 1998).

Information Sheet on Acadian Seaplants Seaweed Extract, Acadian Seaplants Limited, Nova Scotia, Canada, Jan. 8, 1998.

Brochure titled Acadian Seaplants Seaweed Extract Soluble Powder or Liquid, Acadian Seaplants Limited, Nova Scotia, Canada 2000.

Information Sheet titled Product and Technical Information, General Home and Garden Use, Acadian Seaplants Limited, Nova Scotia, Canada (Sep. 5, 1998).

Brochure titled Acadian on Grapes, Grower's Success Series Acadian Seaplants Limited, Nova Scotia, Canada 2000.

Brochure titled Acadian Seaplants Kelp Meal (100% *Ascophyllum nodosum*) For Soil Applications, Acadian Seaplants Limited, Nova Scotia, Canada 2000.

Schmidt, R. E., et al., Proc. 1997 Amer. Forage and Grassl. Counc., Georgetown, TX, 6:158–162.

Coelho, R. W., et al., Proc. 1997 Amer. Forage and Grassl. Counc., Georgetown, TX, 6:163–167.

Allen, V. G., et al., Proc. 1997 Amer. Forage and Grassl. Counc., Counc., Georgetown, TX, 6:168–172.

Saker, K. E., et al., Proc. 1997 Amer. Forage and Grassl. Counc., Georgetown, TX, 6:178–182.

Fike, J. H., et al., Proc. 1997 Amer. Forage and Grassl. Counc., Georgetown, TX, 6:153–157.

HCAPLUS Abstract 1970:517802 of Lemesh, V. F., et al., Navuk 2, 105–109 (1979).

HCAPLUS Abstract 1979:522283 of Jones, R. T., et al. Bot. Mar. 22(6), 393–4 (1979).

HCAPLUS Abstract 1997:229354 of Charreau, B., et al., Transplant. Proc. 29 (1/2), 889–890 (1997).

Hobbs, D., The New Farm May/Jun. 1994, 26–28.

Klober, K., Small Farm Today, 8/96, p. 10.

Hobbs, D., "The Quest for a Water Soluble Mineral".

Hobbs, D., "Kelp Cures Copper".

Morrison, F. B., Fields and Feeding, The Morrison Publish Company, Ithaca, NY (1957), p. 554.

Dennis, S. B., et al., J. Anim. Sci. 76, 2687–2693 (1998).

Fike, J. H., Masters Thesis titled Influence of Seaweed Extract and Other Plant Growth Regulators on Growth, Persistence and Quality of Tall Fescue and Their Potential to Alleviate Tall Fescue Toxicity to Livestock (1995).

Sen, T. L., Seaweed and Plant Growth (1987), pp. 7–4, 7–5.

Buttery, S., Influence of Acremonium Coenophialum on Fescu Arundinacea Growth, Chemical Composition, Digestibility and Tall Fescue Toxicities; Ph.D. dissertation, 1989, abstract and pp. 36, 84 and 86.

Okai, Y., et al., J. Sci. Food Agric. 72, 455–460 (1966).

Okai, Y., et al., J. Sci. Food Agric. 76, 56–62 (1998).

Woodward, L., Vistas, Texas Tech Research, Fall 1999, vol. 8, No. 1, pp. 20–25.

Saker, K. E., et al., J. Anim. Sci. 76, 2694–2700 (1998). pg,15

* cited by examiner

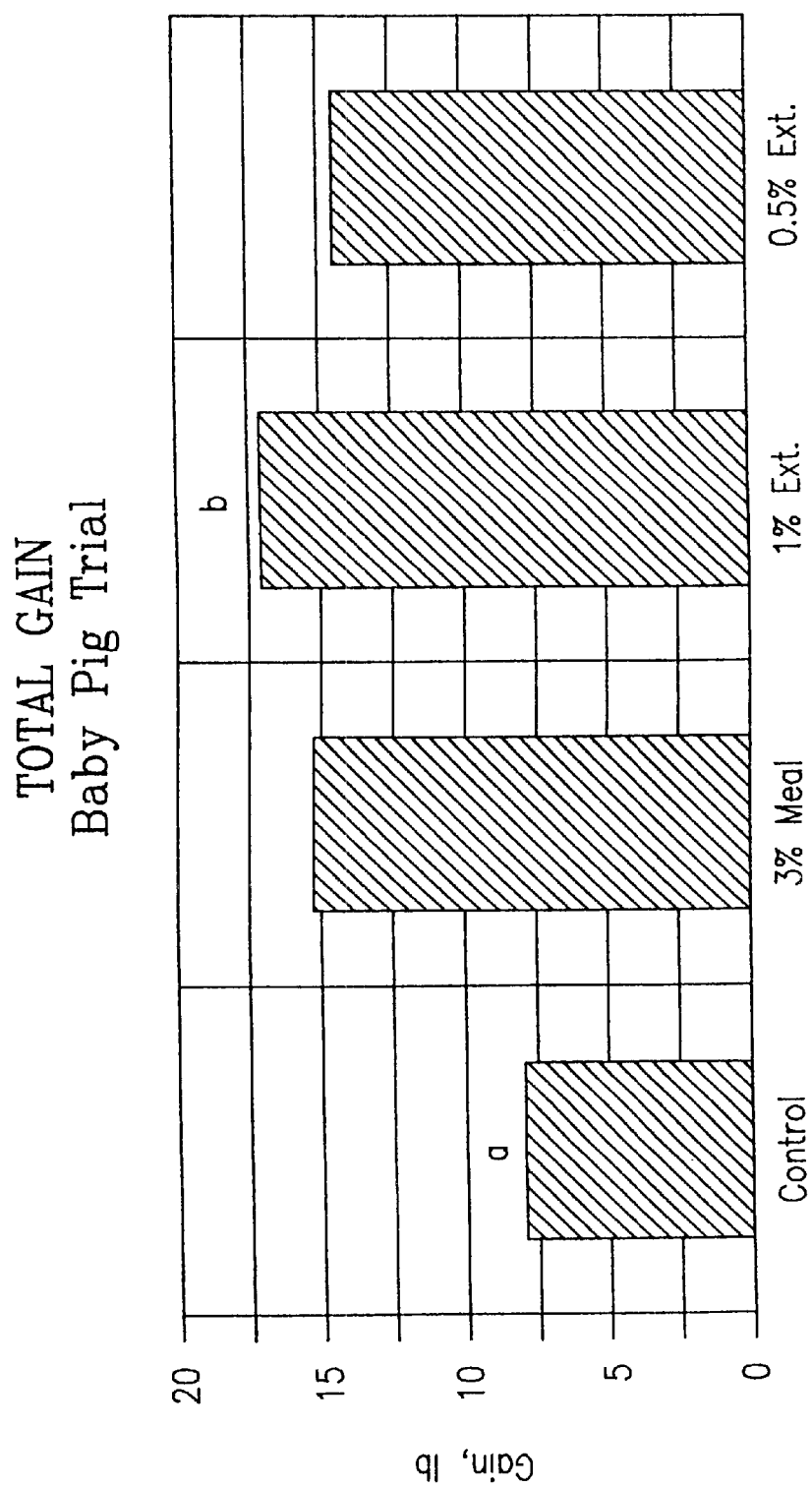

SEAWEED SUPPLEMENT DIET FOR ENHANCING IMMUNE RESPONSE IN MAMMALS AND POULTRY

CROSS-REFERENCE TO RELATED APPLICATIONS

This is a continuation-in-part of U.S. patent application Ser. No. 09/032,104, filed Feb. 27, 1998, now pending.

BACKGROUND OF THE INVENTION

1. Field of the Invention

The invention relates to seaweed and treated seaweed feed supplements for mammal and poultry wherein the host exhibits enhanced immune response. In another aspect, the invention relates to the introduction of seaweed supplement directly to mammal and poultry feed as well as introduction of grazing animals to plants and grasses, which have been pre-treated with seaweed extract. In still another aspect, the invention relates to seaweed feed supplement, which enhances the host immune system for periods beyond cessation of seaweed supplement introduction to the host diet. Aspects of the invention also relate to imparting resistance to Porcine Reproductive and Respiratory Syndrome (PRRS) disease in pigs that have been exposed to PRRS disease and to mitigating the stress of weaning in lactating mares.

2. Description of Related Art

Seaweeds have been used through antiquity in crop production and as early as the 1950's, evidence of plant growth hormones in seaweed was reported. Seaweed is now recognized as a source of plant growth regulators and has been demonstrated to have activity that includes cytokinin, auxin, gibberellin, and idole acetic acid. Seaweed has also long served as feed for domestic and wild animals. Some even graze on seaweed growing on rocky beaches and floating in the ocean water. Seaweeds have been dried and sold as a meal product to be mixed with other feed stuffs. The value of seaweed has been generally attributed to the fact that it is low in carbohydrate and proteins and rich in trace elements; including vitamins B,D,E and vitamin precursors including beta-carotene; and various growth hormones.

Bacterial, fungal, viral and other disease causing agents infect mammals including man, other mammals, plants, insects and poultry. The prevention and control of, for example, diseases have important health and economic implications. Diseases contribute to infections in humans and other mammals including common colds, herpes and cancer and the importance of their control is obvious. Also important is control of agent diseases in mammals and poultry for economic reasons as well as the ability of such mammals and poultry to become disease reservoirs or carriers, which facilitate the spreading of diseases to other host including humans. Plant diseases have been known to have a disruptive effect on the cultivation of fruit trees, tobacco and various vegetables as well as the utilization of plant leaves and grasses by grazing animals.

The prevention and control of diseases is thus of prime importance to man, other mammals and poultry; considerable research has been devoted to anti-disease measures. Prior research efforts have described water soluble extracts from marine red algae selected from the group consisting of Turnerella mertensiana, Schizymenia epiphytic, Turnerella pennyi and mixtures thereof as effective to inhibit the growth of herpes simplex virus, Type 1 and Type 2 and herpes zoster and to relieve the pain caused by infection attributable to such viruses.

Applications of materials containing high concentration of hormones reduced plant stress and enhance plant tolerance to drought and salinity. Seaweed, an excellent source of cytokinins and auxins has been associated with enhanced root development of grasses grown under stress environments. Concentration of antioxidants increase significantly in response to exogenous seaweed treatments. Increase of these antioxidants had been correlated with photosynthetic capacity of plants subject to environmental stress.

So far as animals are concerned, seaweed supplements have been described as providing increased nutritional value.

When animals, mammals and poultry are grown for food production, there is generally a loss of a small but constant percentage of the animals prior to bringing the animals to the market which may be due to lack of nutrients, sickness, improper growing temperature and the like. This means that the feed eaten prior to death of the animals and other costs expended on the animals, which do not survive, are wasted. In addition, animals consuming costly feed for fattening which have lowered immune systems also waste the cost of the feed and decreases the weight gains of poultry and mammals and thus their economic value.

SUMMARY OF THE INVENTION

It has now been found that seaweed supplement, both meal and water-soluble extract forms of seaweed, enhance immune responses in mammals and poultry when introduced into the host diet either directly, or indirectly through plants including forages.

The invention is directed to use of seaweed supplement, for example, from *Ascophylum nodosum,* to improve immune response in mammals and poultry. When the seaweed supplement is included as a pasture treatment or feed ingredient for ruminant and non-ruminant animals, poultry, and other mammals, the immune function is enhanced and health of the host is improved. Studies show sheep that grazed treated forage had increased blood levels of vitamin A and selenium indicating that the anti-oxidant activity had been increased in the host as well as plants that the mammals grazed. In addition, influence of the seaweed supplement on steers that grazed forage infected with the fungus, known to result in several animal disorders, provided further evidence that the steers that grazed the treated forage responded with increased anti-oxidant activity and that the steers had improvement in their immune function. Steers that grazed the fungus infected forage had depressed immune function that treatment with seaweed extract was able to reverse and to restore to normal levels. Further the improved immune function achieved by the cattle grazing on the aforementioned pasture was retained through feedlot finishing even without continuation of the seaweed supplement being furnished to the diet. The invention was also productive in providing grazing lambs improved antioxidant function, daily gains and total gains as compared to control lambs grazing non-treated pastures.

An independently inventive embodiment is directed to imparting resistance to PRRS disease in pigs that have been exposed to PRRS disease and comprises administering a PRRS disease resistance imparting effective amount of seaweed supplement to the pigs. Weaned pigs stressed by exposure to PRRS disease present within the swineherd were fed different amounts of seaweed extract or seaweed meal. The seaweed extract and meal were effective in improving the health of the pigs resulting in increased feed intake, growth rates (higher daily and total gains) and improved feed conversion (feed:gain ratio). No pigs fed the extract or meal died while three deaths occurred within the control group.

Another independently inventive embodiment is directed to mitigating the stress in lactating mares during and after weaning when the lactating mares are physically separated from their foals and comprises prior to weaning administering to the lactating mares a weaning stress mitigating effective amount of seaweed supplement. Lactating mares fed seaweed supplement prior to weaning had a substantially constant neutrophil to lymphocyte ratio for 40 days and longer after weaning whereas lactating mares in the control group (not fed seaweed supplement) had neutrophil to lymphocyte ratios that were more than double at 28 days after weaning.

Improvement in immune function for mammals and poultry has large implications in the field of mammal and poultry health. Improvement in immune function in swine may well indicate applications to human health and immune function as well. Improved carcass characteristics were shown by cattle, which grazed on forage treated with seaweed extract. The monetary benefits to the industry will be significantly impacted in the positive from producing foraging animals wherein the forage has been treated by seaweed extract. Furthermore, the seaweed treatment of fescue, for example, infected with the fungus can at least offset the negative effects on immune function and will improve animal performance during the final finishing periods, ie., feedlots. Since fescue is a major pasture grass in much of the livestock producing areas of the eastern United States, the implications are far reaching.

The term administering seaweed supplement is used herein to encompass both direct feeding of seaweed supplement in the diet and also feeding as a result of grazing on seaweed supplement treated pastures including seaweed extract treated pastures and seaweed meal treated pastures.

BRIEF DESCRIPTION OF THE DRAWINGS

FIG. 9 is a graphic presentation of baby pig trial total gain for control, 3% seaweed meal, 1% seaweed extract, and 0.5% seaweed extract, showing results of Example V.

DETAILED DESCRIPTION

Figure 1:
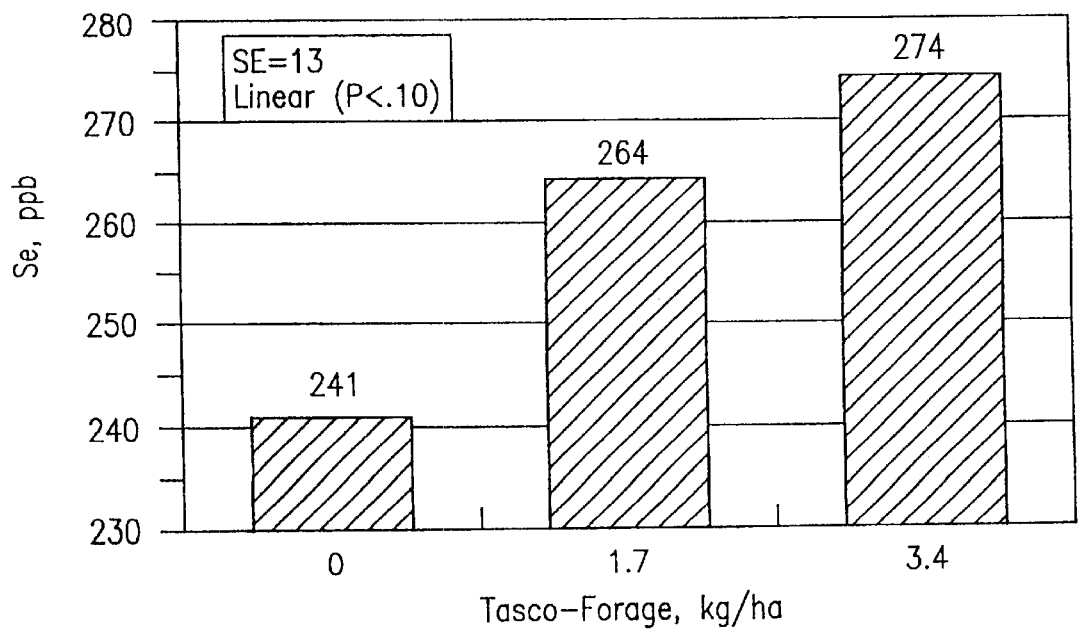
FIG. 1 is a graphic presentation of the effect of seaweed on lamb whole blood, selenium showing results of Example I.

We turn firstly to the broadest form of the invention; ie., a method of enhancing immune response in mammals comprising administering seaweed supplement to the mammal in amounts ranging from about 0.01% to about 3.0% or even to about 5% by weight of the diet or greater for a period of about 3 to about seven days, e.g., for 14 days, or longer.

The seaweed supplement is, for example, seaweed extract or seaweed meal.

The seaweed from which the seaweed supplement is obtained can be from any of the various seaweed plant classifications, preferably those that have been utilized in agriculture and include seaweeds from the plant orders Laminariaceae, Fucaceae and Gigartinaceae. Genus groups include Ascophyllum, Laminaria, Durvillea, Macrocystis, Chondrus and Ecklonia. The seaweed for the preferred seaweed supplement herein is from the genus Ascophyllum which belongs to the order Fucaceae and is *Ascophyllum nodosum*. *Ascophyllum nodosum* is a brown seaweed which grows along the North Atlantic shorelines of Canada, the United States, and Europe.

We turn now to seaweed supplement which is seaweed extract.

Seaweed extract is water soluble and can be obtained by alkaline hydrolysis extraction. A preferred seaweed extract is obtained by alkaline hydrolysis extraction from *Ascophyllum nodosum*; commercial products of this kind are available from Acadian Seaplants Limited of Nova Scotia Canada, and are sold under the tradenames Acadian Soluble Seaweed Extract Powder (powder form), Acadian Liquid Seaweed Concentrate (liquid form), Tasco™-Ex (powder form) and Tasco™-Forage (powder form). Acadian Soluble Seaweed Extract Powder, Tasco™-Ex and Tasco™-Forage have the same composition. Acadian Soluble Seaweed Extract Powder is made up of brownish-black crystals, has a seaweed-like odor, is 100% soluble in water and has a pH of 10–10.5 in water and typical analysis shows by weight 6.5% maximum moisture, 45–55% organic matter, 45–55% ash (minerals), 1.0–2.0% total nitrogen (N), 2.0–4.0% available phosphoric acid ($P_2O_5$), 18.0–22.0% soluble potash ($K_2O$), 1.0–2.0% sulfur (S), 0.2–0.5% magnesium, 0.1–0.2% calcium, 3.0–5.0% sodium, 75–150 ppm boron, 75–250 ppm iron, 8–12 ppm manganese, 1–10 ppm copper, 25–75 ppm zinc; alginic acid, mannitol, and laminarin carbohydrates; cytokinin, auxin and gibberellin growth promoters; and the following average grams of amino acid per 100 grams of protein: alanine, 3.81; arginine, 0.22; aspartic acid, 5.44; cystine, trace; glutamic acid, 7.69; glycine, 3.16; histidine, 0.42; isoleucine, 1.94; levcine, 4.84; lysine, 1.33; methonine, 1.39; phenylalanine, 2.82; proline, 4.42; serine, 0.14; threonine, 1.27; tyrosine, 1.80, and valine, 3.46.

Seaweed extract is preferably applied to pasture forage as a water solution at the beginning of the grazing season and in the middle of the grazing season. The seaweed extract can be applied, for example, in an amount ranging from 0.3 kg/ha to 5 kg/ha, e.g., 1 to 4 kg/ha, and an application amount of 3.4 kg/ha (3 lbs/acre) has been used with good advantage. The seaweed extract (powder form) is readily dissolved in 20 to 40 gallons of water per acre. Application is preferably carried out by spraying the water solution on the pasture forage using a commercial field-type of sprayer.

Seaweed extract is preferably admixed into diet for direct feeding by inclusion at the time of feeding by top dressing or mixing into the feed at the time of feeding or by premixing at the time the diet ingredients are combined and is included in an amount of, e.g., 0.01 to 3% by weight (powder or liquid concentrate commercial products) of the diet.

We turn now to seaweed supplement which is seaweed meal or flour.

The seaweed meal or flour can be obtained by dehydrating the seaweed, for example, by solar drying followed by low heat finish drying and processing the dehydrated material into a granular meal or four. A preferred seaweed meal is obtained from *Ascophyllum nodosum* and is available from Acadian Seaplants Limited of Nova Scotia, Canada, and is sold under the tradenames Acadian Kelp Meal and Tasco™-14. Acadian Kelp Meal and Tasco™-14 have the same composition. A typical analysis of Acadian Kelp Meal shows the following approximate weight percentages: moisture 12.0%, crude protein 6.0%, crude fiber 6.0%, ash (minerals) 22.0%, fat 20%, and carbohydrates 52.%. Analysis of Acadian Kelp Meal for carbohydrates gives by weight 18.0–27.0% alginic acid, 3.8–8.0% mannitol, 2.0–5.0% laminarin, and 20.0–22.0% other sugars. Analysis of Acadian Kelp Meal for minerals gives 50–150 ppm aluminum, 5–15 ppm barium, <1 ppm beryllium, 80–100 ppm boron, <1 ppm cadmium, 1.0–3.0% calcium, 1.0–3.0% chloride, 1–2 ppm chromium, <1 ppm cobalt, 1–10 ppm copper, <1,000 ppm iodine, 100–500 ppm iron, <1 ppm lead, 0.5–1.0% magnesium, 10–50 ppm manganese, <1 ppm mercury, <2 ppm molybdenum, <1 ppm nickel, 0.5–2.0% nitrogen, 0.1–0.2% phosphorus, 1.5–2.5% potassium, 3–4 ppm selenium 2.4–4.0% sodium, 100–600 ppm strontium, 2.0–3.0% sulfur, <10 ppm tin, 1–10 ppm titanium, 2–6 ppm vanadium and 10–50 ppm zinc. Analysis of Acadian Kelp Meal for vitamins gives 0.1–0.4 ppm biotin, 30–60 ppm carotene, 0.1–0.5 ppm folic acid, 0.1–0.5 ppm folinic acid, 10–30 ppm niacin, 5–10 ppm riboflavin, 1–5 ppm thiamin, 150–300 ppm tocopherols, 100–2,000 ppm vitamin C, <0.004 ppm vitamin $B_{12}$, and <10 ppm vitamin K. Analysis of the amino acid content for Acadian Kelp Meal gave the following expressed as grams of amino acid per 100 g of protein nitrogen: alanine 5.3, arginine 8.0, aspartic acid 6.9, cystine (trace), glycine 5.0, glutamic acid 10.0, histidine 1.3, isoleucine 2.8, leucine 4.6, lysine 4.9, methionine 0.7, phenylalanine 2.3, proline 2.6, serine 3.0, threonine 2.8, tryptophan (trace), tyrosine 0.9, and valine 3.7.

Seaweed meal is preferably applied to a pasture to provide seaweed treated forage by application in dry form and solubles from seaweed meal dissolve after application so that the solubilized material is available for foliar uptake and/or leaches into the ground and is taken up by the forage. The seaweed meal can be applied, for example, in an amount of 0.3 to 10 kg per acre.

Seaweed meal is preferably admixed into diet for direct feeding by inclusion at the time the diet ingredients are mixed or by directed addition at the time of feeding, in an amount of e.g., 0.01 to 5%, by weight of the diet.

In one embodiment herein, mammals, e.g., cattle or lambs, are grazed on seaweed supplement treated endophyte-infected forage, e.g., endophyte-infected tall fescue, whereby immune function is preserved or depressed immune function is reversed by the seaweed supplement treatment.

Livestock grazing tall fescue infected with an endophyte, e.g., *Neotiphodium coenophialum*, exhibit several disorders collectively referred to as "Fescue Toxicity." The endophyte may influence mineral composition of the plant and mineral metabolism in the animal. Cattle grazing endophyte infected tall fescue exhibited signs of Cu deficiency. Selenium and vitamin E have been investigated in relation to fescue toxicity although results have been inconsistent. It was found that lambs grazing endophyte infected tall fescue treated with seaweed extract show increased whole blood Se and serum vitamin A. Thus, the relationships of endophyte and seaweed extract on performance and mineral status of steers were investigated.

Tall fescue is one of the most important forages grown and it is used widely because it is highly productive and resistant to a number of stresses. Most tall fescue is infected with a fungus, which lives inside the plant. The plant provides a home to the fungus, and the fungus helps the plant to tolerate stresses such as drought and insects. However, animals which graze infected fescue often have lowered immune system response, low weight gain, reduced milk production, lowered conception rates and other health problems. The possibility was reviewed that the quality of tall fescue could be improved and its toxicity reduced by use of plant growth regulators. Seaweed extract is known to contain plant growth regulating compounds, and it was applied to tall fescue.

The seaweed supplement and amounts thereof for the embodiment where mammals are grazed on seaweed supplement treated endophyte infected forage, are the same as described above in relation to the broadest form of the invention with the seaweed supplement being applied to the pasture forage as described above to provide the seaweed supplement treated endophyte infected forage.

In an independently inventive embodiment, pigs that are exposed to PRRS disease are administered a PRRS disease resistance imparting effective amount of seaweed supplement. As indicated above, the seaweed supplement has been found to improve the health of the pigs resulting in increased feed intake, growth rates and improved feed conversion compared to where the pigs are not fed seaweed supplement.

The swine industry in the United States has moved largely to confinement operations with large concentrations of hogs produced by relatively few operators. Swine health, while always important, takes on greater urgency when large numbers of hogs are housed in close proximity as is usually the case now. Porcine Reproductive and Respiratory Syndrome (PRRS) was an unrecognized viral disease of swine until described in the United States in 1987. Within herds, the disease spreads rapidly with up to 95% of pigs affected within two to three months. The primary mode of transmission is by relatively close contact among pigs but the virus can also be spread aerially and through semen from infected boars. The disease is characterized by abortion, premature farrowing, stillborn and mummified pigs, and respiratory disease with chronic poor performance of nursing and weaning pigs but affects pigs of any age. Of major economic importance, PRRS disease is thought to affect more than two-thirds of the herds in the United States.

For imparting resistance to PRRS disease, the seaweed supplement is preferably fed directly to the pigs in admixture with diet. Both seaweed extract and seaweed meal forms of seaweed supplement are useful in this embodiment. Admixture into diet is readily carried out as described above for the broadest embodiment herein. As indicated above, the seaweed supplement is fed in a PRRS disease resistance imparting effective amount. When seaweed extract is the seaweed supplement, it is fed, for example, in an amount, for example, of 0.01 to 3% by weight (powder or liquid concentrate forms of seaweed extract) of the diet. When seaweed meal is the seaweed supplement, it is fed, for example, in an amount of, e.g., 0.1 to 5%, by weight of the diet. The seaweeds described above in conjunction with the broadest form of the invention are useful to provide seaweed supplement for this embodiment and preferably the seaweed supplement is from *Ascophyllum nodosum*. The seaweed supplement is continued in the diet, preferably, for the period where PRRS disease resistence is important.

A special case herein is directed to baby pigs (castrated males and females) that have been exposed to PRRS disease and are placed in the nursery on weaning. These pigs are placed in the nursery normally at age 21–35 days and are ordinarily maintained there for a five week nursery phase. Including seaweed supplement in diets over the entire nursery period for baby pigs that had been exposed to PRRS disease has been found to provide healthier pigs with higher daily, weekly and total weight gains, higher body weights and improved feed conversion (lower feed to gain ratios) compared to control pigs, that is, where the pigs are not fed seaweed supplement. Whereas the rate of weight gain steadily increases for the treated pigs, the rate of weight gain decreases after week 3 of the nursery phase for control pigs. Thus, the feeding of seaweed supplement has been indicated to improve the ability of disease-stressed baby pigs to overcome the disease challenge and improve in performance.

We turn now to the embodiment where the stress of weaning is mitigated in lactating mares during and after weaning when the lactating mares are physically separated from their foals by treatment comprising prior to weaning administering to the lactating mares a weaning stress mitigating effective amount of seaweed supplement.

Recently there has been a particular interest in how stress-related physiological changes impinge upon immune function. The end of lactation (milk production) has components of both a physiological and psychological stress. At weaning the young foal is removed from its mother which is still responding physiologically by producing milk. The mother may still be able to see and hear her foal, which, along with the physical separation creates anxiety in both the mother and foal. Such anxiety stresses the mares and affects the immune response of the mares by decreasing the number of lymphocytes resulting in increased neutrophil to lymphocyte ratio. This effect is caused by stress hormones. The principal stress hormone, cortisol, has been shown to cause a shift in the number of various white blood cells causing increase in neutrophil to lymphocyte ratio and decreasing immune response. This embodiment stabilizes the neutrophil to lymphocyte ratio and prevents significant increase thereof in mares after weaning thereby mitigating the stress of weaning.

For mitigating the stress of weaning in lactating mares, feeding of the seaweed supplement is preferably started at least five days prior to weaning, very preferably at least 10 days prior to weaning or 10 to 30 days prior to weaning, e.g., starting 14 days prior to weaning, and is preferably continued until weaning occurs or even after weaning occurs, e.g., up to seven days after weaning occurs.

The seaweed supplement is directly fed to the mares in admixture with the diet or is applied to pasture forage consumed by the mares, as described above for the broadest embodiment herein. As indicated above, the seaweed supplement is administered in a weaning stress mitigating effective amount as indicated by stabilization of neutrophil to lymphocyte ratio to an increase of less than 40% or even a decrease, e.g., of up to 20 or 30%. For direct feeding, admixture with the diet is readily carried out as described above and when the seaweed supplement is seaweed extract, it is fed, for example, in an amount, for example, of 0.01% to 3% by weight (powder or liquid concentrate forms of seaweed extract) of the diet and when the seaweed supplement is seaweed meal, it is fed, for example, in an amount of, for example, 0.01 to 5% by weight of the diet. The seaweeds described above in conjunction with the broadest form of the invention are useful to provide the seaweed supplement for this weaning stress mitigating embodiment, and preferably the seaweed supplement is from *Ascophyllum nodosum*.

The invention is illustrated by the following examples.

EXAMPLE I

Thirty-two wether lambs (Dorset ×Rambouillet ×Finn) grazed endophyte-infected (70%) tall fescue during two experimental periods (26 and 21 days). Lambs were blocked by weight, randomized within blocks, and assigned to one of three seaweed treatments in a complete randomized block design with four replications/treatment. Seaweed extract (Tasco™-Forage) treatments, applied foliarly on April 5 and June 20, were 0, 1.5, and 3.0 lb acre. Paddocks were 0.09 acre in size. Lambs had access to water and NaCl blocks at all times. Lambs were grazed during two periods: May 21 – June 17 (26 days) and July 21 –August 10 (21 days). Lambs were weighed and blood was collected by jugular puncture at the beginning and end of each trial period. Lambs were weighed and re-randomized to treatments four days prior to Period 2.

Samples to determine forage mass and nutritive value were taken prior to initiation of each period and 31 days after the end of Period 2. Forage mass samples also were taken at the end of each period. All paddocks were mowed at the end of the Period 1 to equilibrate forage mass per paddock. Samples were analyzed for concentrations of neutral detergent fiber (NDF), acid detergent fiber (ADF), hemicellulose, cellulose, lignin, crude protein, and total nonstructural carbohydrate. In vitro dry matter digestibility also was determined on the samples. Forage was also analyzed for pyrolizidine (University of Kentucky, Lexington, Ky.) and ergot (Auburn Fescue Diagnostic Laboratory, Auburn, Ala.) Alkaloids. For Period 2, serum was analyzed for vitamins A and E, and whole blood was analyzed for Se (VA-MD College of Veterinary Medicine). Plant and serum minerals were determined by inductively coupled plasma spectrometry.

Figure 2:
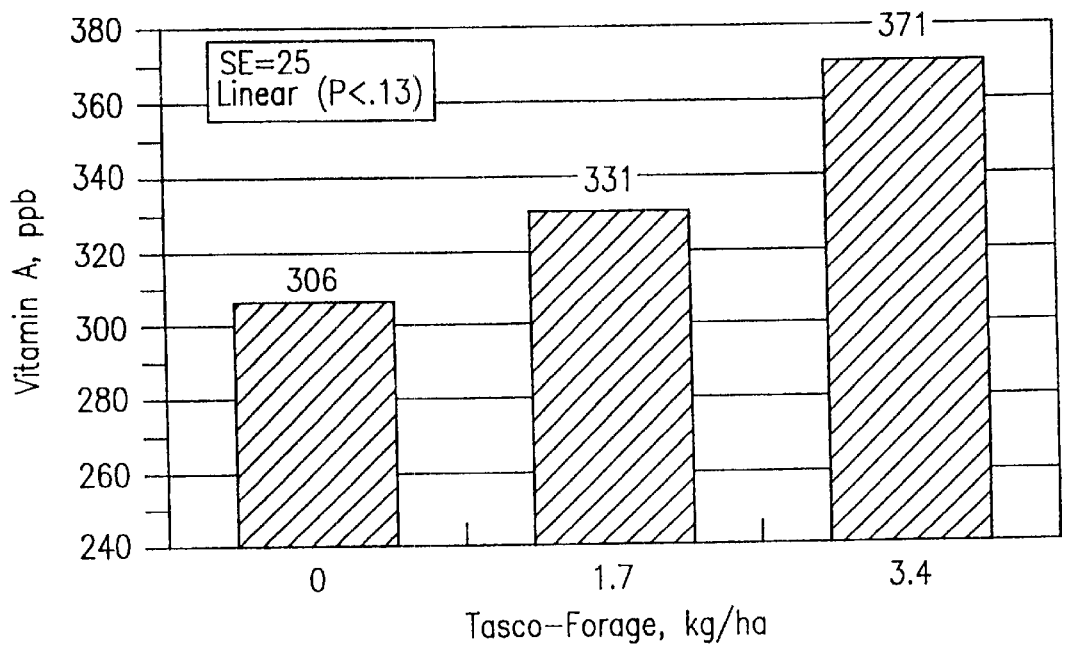
FIG. 2 is a graphic presentation of the effect of seaweed on lamb serum vitamin A, showing results of Example I.

During Period 1, lambs grazing forage treated at the high seaweed extract rate maintained weight while control lambs lost weight (Table 1). Lambs grazing treated forage had greater daily gains in Period 2 than did wethers on control pastures. No effect of treatment was seen on serum vitamin E concentrations, but serum vitamin A increased linearly (FIG. 2). Selenium in whole blood (measured after Period 2 only) was increased linearly by seaweed extract treatment (FIG. 1). An increase in selenium likely indicated an increase in glutathione peroxidase in the animal.

TABLE 1

Influence of seaweed extract (SWE) on average daily gain, serum vitamin A, and whole blood Se of wether lambs grazing endophyte-infected tall fescue.

| Item | SWE, lb/acre | | | |
|---|---|---|---|---|
| | 0 | 1.5 | 3.0 | S.E. |
| Period 1 | | | | |
| Average daily gain, lb/d | −.07 | −.11 | 0 | .07 |
| Period 2 | | | | |
| Average daily gain, lb/d[a] | .07 | .26 | .24 | .07 |
| Serum vitamin A, ppb[b] | 306 | 331 | 371 | 25 |
| Whole blood Se, ppb[c] | 241 | 264 | 274 | 13 |

[a]Indicates difference between control vs. the mean of SWE treatments (P ≦ .05).
[b]Linear effect of SWE (P ≦ .13).
[c]Linear effect of SWE (P ≦ .10).

Seaweed treatment of infected tall fescue increased antioxidant activity in the animal, a first step toward the potential to alter immune function and animal health.

Lambs grazing seaweed extract treated forage had greater weight gains and also had increased concentrations of vitamin A and selenium in their blood.

The results show that seaweed extract treatment of tall fescue improves production of animals grazing the tall fescue and that seaweed extract is helpful in reducing tall fescue toxicity.

EXAMPLE II

Forty-eight yearling Angus and Angus X Hereford steers were randomized to four paddocks of E+ (80%) and four paddocks of E− (<5%) Ky-31' tall fescue at Glade Spring, Va. in 1995, 1996 and 1997 for a total of 144 steers. Forty-eight yearling ¾ Angus X ¼ Brahman steers were randomized to four paddocks of E+ (100%) and four paddocks of E− (<5%) Ky-31' tall fescue at Prairie, Miss. in 1996 and 1997 for a total of 96 steers. At each location, two paddocks of E+ and two paddocks of E− tall fescue were sprayed with seaweed extract (*A. nodosum;* Tasco™-Forage, Acadian Seaplants Limited, Dartmouth, Nova Scotia, Canada) at 3 lb/acre before steers began grazing in April and again in mid-summer. At both locations, steers grazed continuously from April until October. Steers were weighed and rectal temperatures were recorded initially, every 28 days, and at the end of the grazing season. All cattle received standard health care including immunization for Pasteurella hemoletica, Infectious Bovine rhinotrachetis, Bovine Virus Diarrhea, Clostridia perfringes C&D and were treated with Ivomec for internal parasites. Blood samples were taken by jugular vena puncture initially, and in May, July, and September for analysis of serum minerals and vitamin A Pastures were sampled each time cattle were weighed for forage mass by clipping two 20-ft strips/paddock, and samples for mineral analysis were taken by diagonally walking each paddock and sampling fescue every 20 ft.

Concentrations of minerals were determined in fescue and in blood serum by measuring atomic emission with an inductively coupled plasma spectrometer after digestion with nitric and perchloric acids. Green leaves of tall fescue were collected from within each pasture in Virginia at 28 day intervals beginning in April and ending in November for determination of (superoxide dismutase) SOD activity. In Mississippi green leaves were collected from each pasture in July, September and October in 1996 and at 28-day intervals in 1997. These samples were frozen in liquid N in the field and were stored in a freezer at 100 degrees Fahrenheit until SOD activity was measured. Samples collected in Mississippi were transported to Virginia in liquid N and were analyzed as described previously. Phagocytic activity and monocyte major histocompatibility complex Class II expression 6 (MHC Class II) of the monocyte cell population was measured using a cell-bound fluorochrome detected through flow cytometry. Data were analyzed using an ANOVA.

Immune response was influenced by treatments. Total leukocyte counts were increased in Virginia steers grazed on seaweed extract treated endophyte infected fescue compared to non-treated endophyte-infected fescue, and this was particularly evident in July and August. However, the endophyte free group of steers demonstrated the highest leukocyte counts of all treatment groups. Cell function appeared to be influenced by seaweed extract treatment. In general, application of seaweed extract to endophyte infected fescue enhanced immune response in grazing steers and in both endophyte infected and endophyte-free groups during cross-country transport to the feedlot. Antioxidant activity in response to seaweed extract, particularly SOD, a Cu-dependent enzyme, may have influenced the immunocompetence of these steers directly by increasing steer SOD concentrations or indirectly as a source of bioavailable copper in the diet to enhance monocyte function.

Increased immune function in cattle that grazed seaweed treated pastures (both infected and non-infected fescue) remained with cattle during transportation to the feedlot and throughout the 132 day finishing period. Carcass evaluation showed that cattle that had grazed the seaweed treated pastures had USDA carcass grades that were about ½ a grade higher than cattle not exposed to seaweed. Furthermore, an increase in marbling of the meat was indicated.

Results are shown in FIGS. 3a, 3b, 3c, 3d, 4a, 4b, 5 and 6.

Figure 3A:
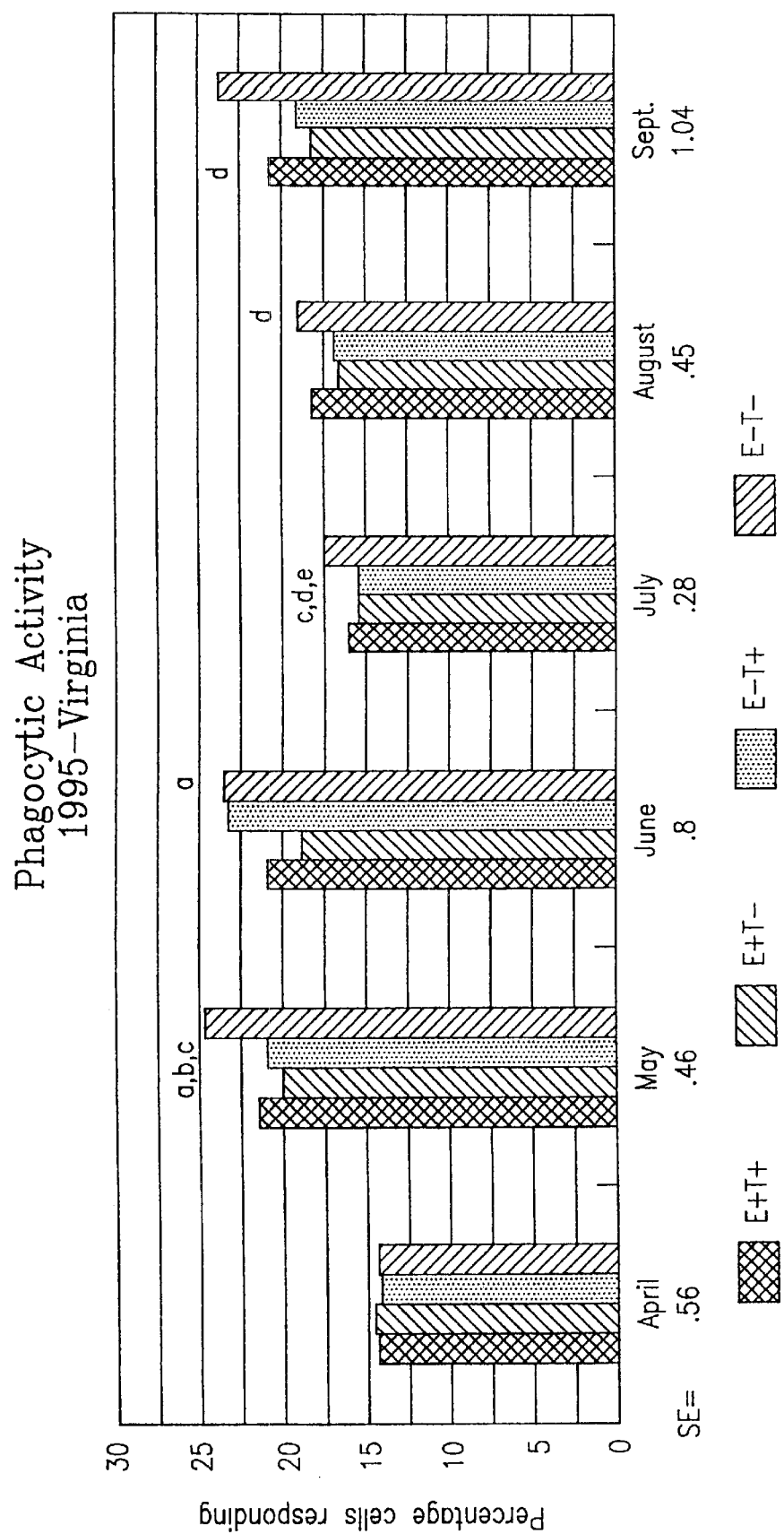
FIG. 3a is a graphic presentation of the effect of seaweed extract and endophyte infection on immune cell response (phagocytic activity) of steers grazing tall fescue in 1995, showing results of Example II.

In FIG. 3a, "a" indicates an endophyte effect (P<0.05), "b" indicates an endophyte by Tasco™ interaction (P<0.01), "c" indicates a Tasco™ effect (P<0.08), "d" indicates an endophyte by Tasco™ interaction (P<0.05) and "e" indicates an endophyte effect (P<0.06), and n=2 for each mean where pasture is the experimental unit.

Figure 3B:
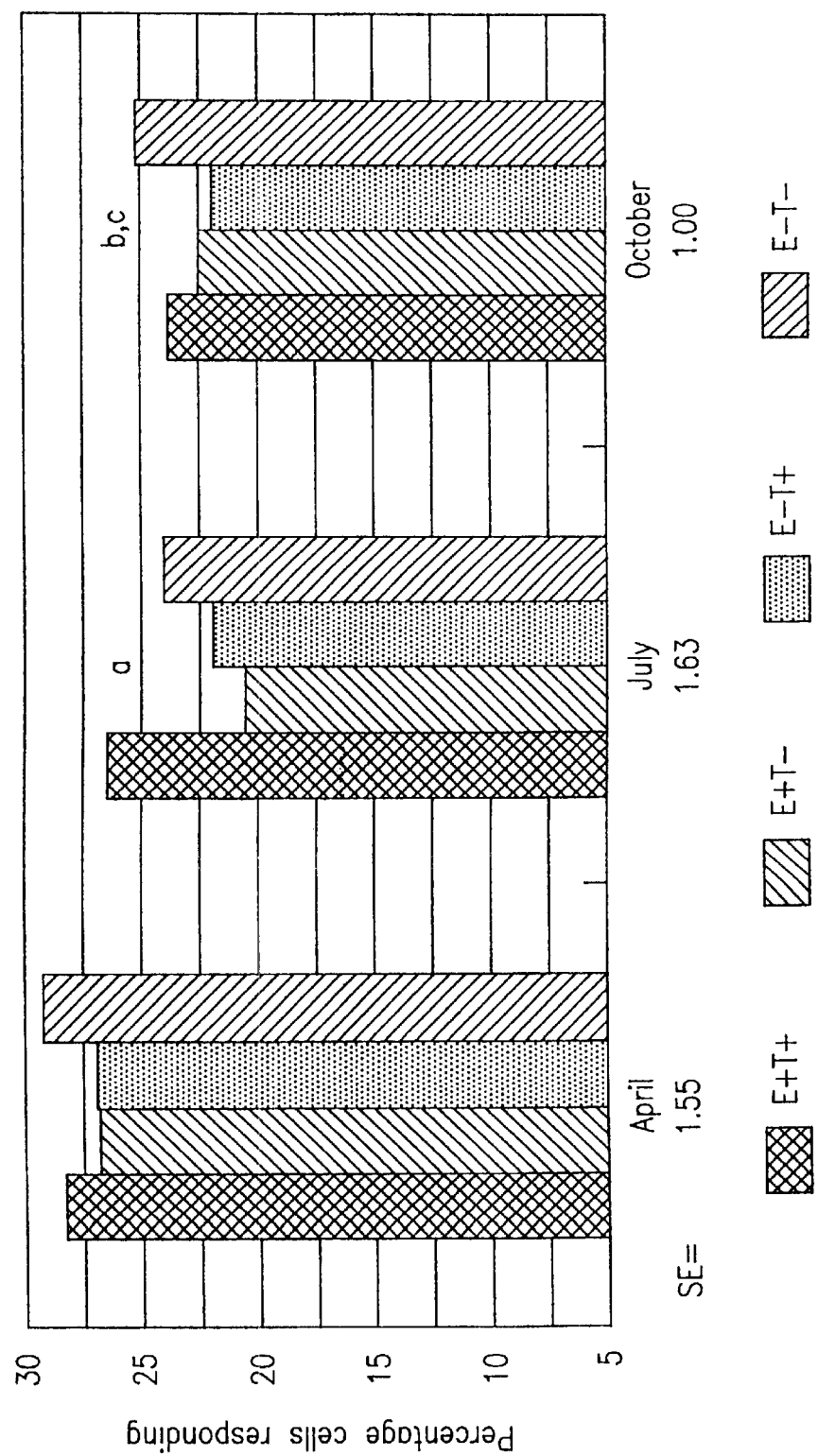
FIG. 3b is a graphic presentation of the effect of seaweed extract and endophytic infection on immune cell response (phagocytic activity) of steers grazing tall fescue in 1996 and 1997, showing results of Example II.

In FIG. 3b, "a" indicates a Tasco™ by endophyte interaction (P<0.05), "b" indicates a Tasco™ by endophyte interaction (P<0.01) and "c" indicates a location by Tasco™ by endophyte interaction (P<0.05), and n=12 for each mean where pasture is the experimental unit.

Figure 3C:
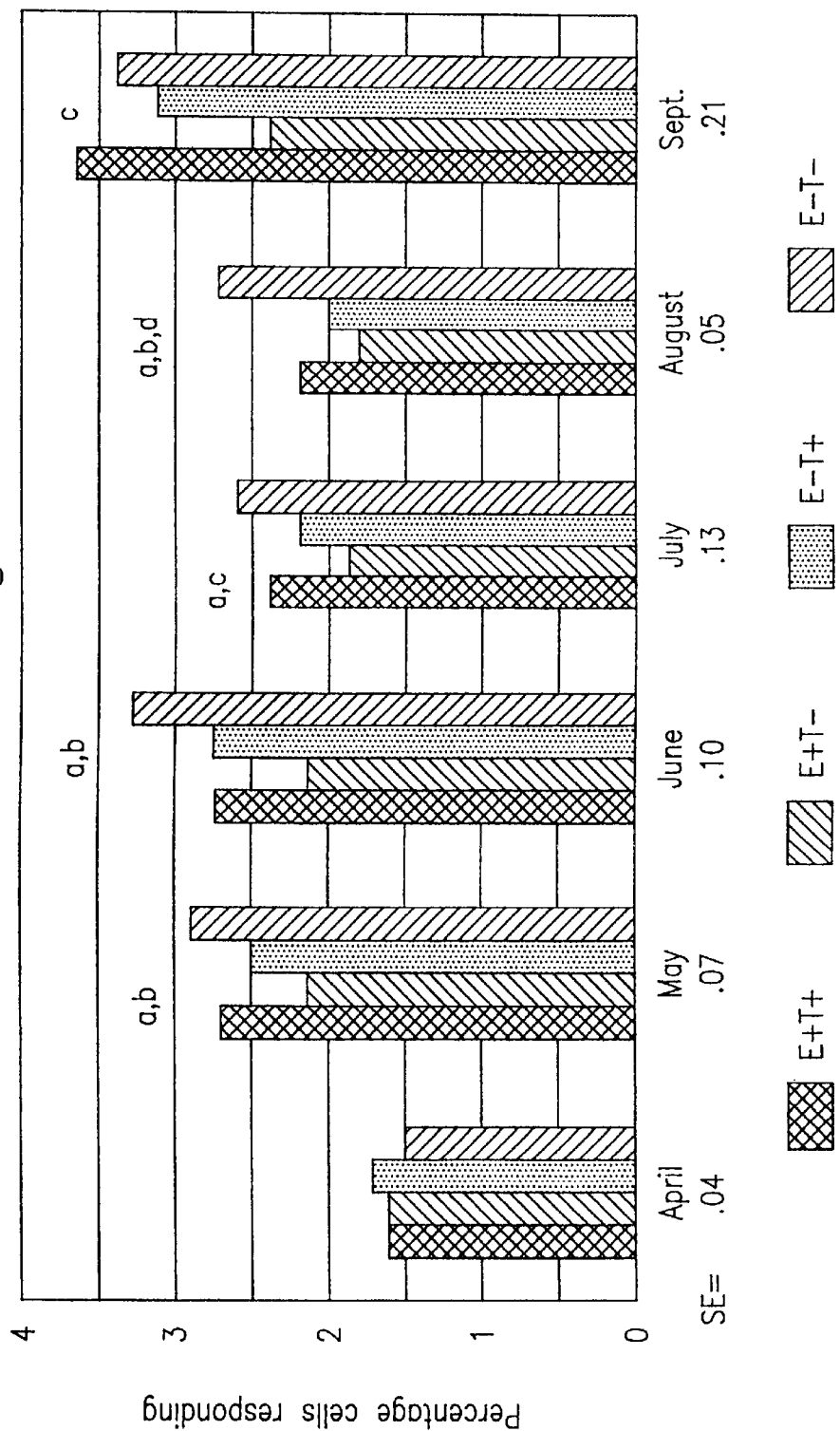
FIG. 3c is a graphic presentation of the effect of seaweed extract on immune function as measured by monocyte major histocompatibility complex Class II expression (MHC Class II Activity) of steers grazing tall fescue in 1995, showing results of Example II.

In FIG. 3c, "a" indicates an endophyte effect (P<0.05), "b" indicates an endophyte by Tasco™ interaction (P<0.01), "c" indicates an endophyte by Tasco™ interaction (P<0.05) and "d" indicates a Tasco™ effect (P<0.08), and n=2 for each mean where pasture is the experimental unit.

Figure 3D:
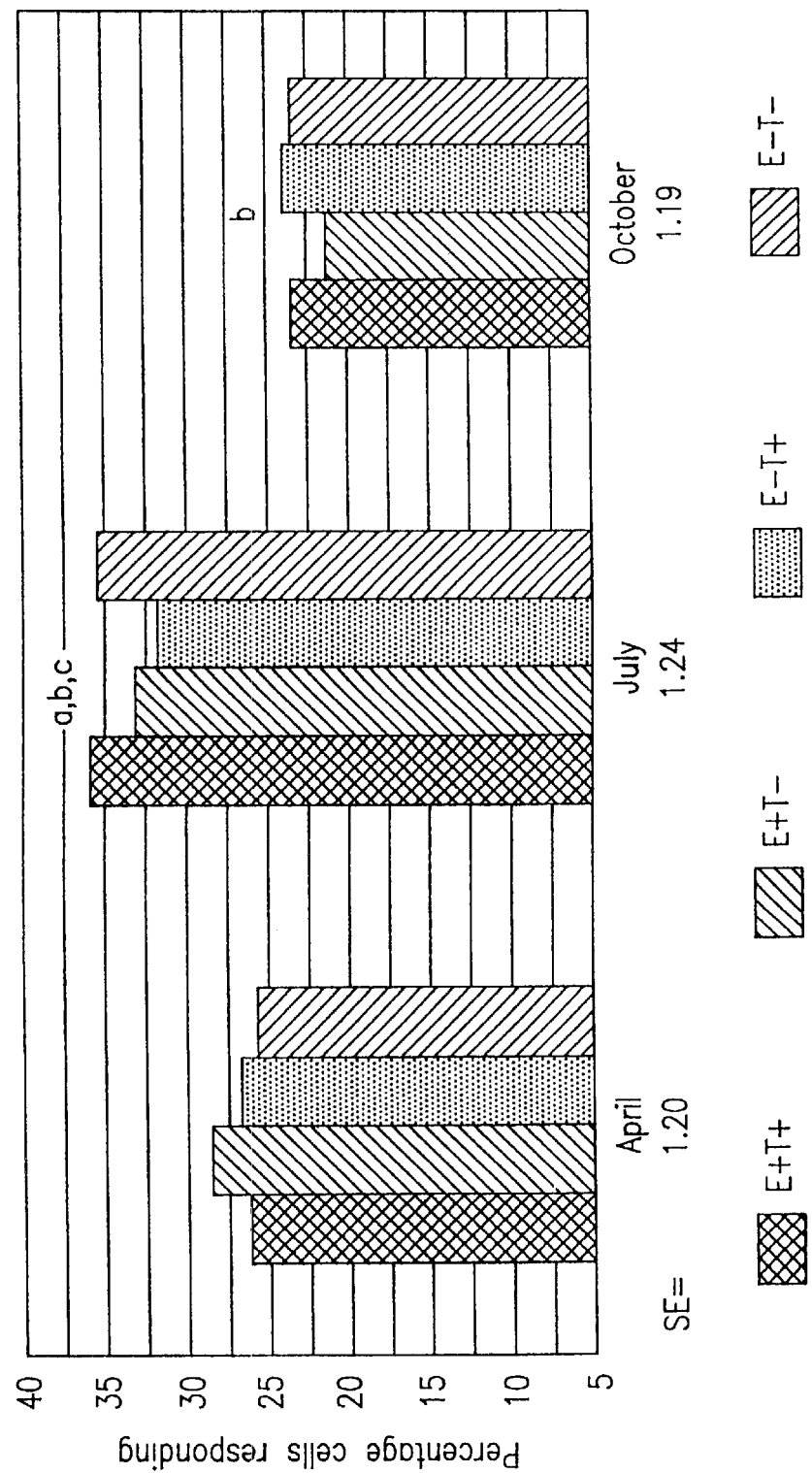
FIG. 3d is a graphic presentation of the effect of seaweed extract on immune function as measured by monocyte major histocompatibility complex Class II expression (MHC Class II Activity) of steers grazing tall fescue in 1996 and 1997 and shows results of Example II.

In FIG. 3d, "a" indicates a Tasco™ by endophyte interaction (P<0.05), "b" indicates a Tasco™ by copper interaction (P<0.05) and "c" indicates a location by endophyte interaction (P<0.05), and n=12 for each mean where pasture is the experimental unit.

Figure 4A:
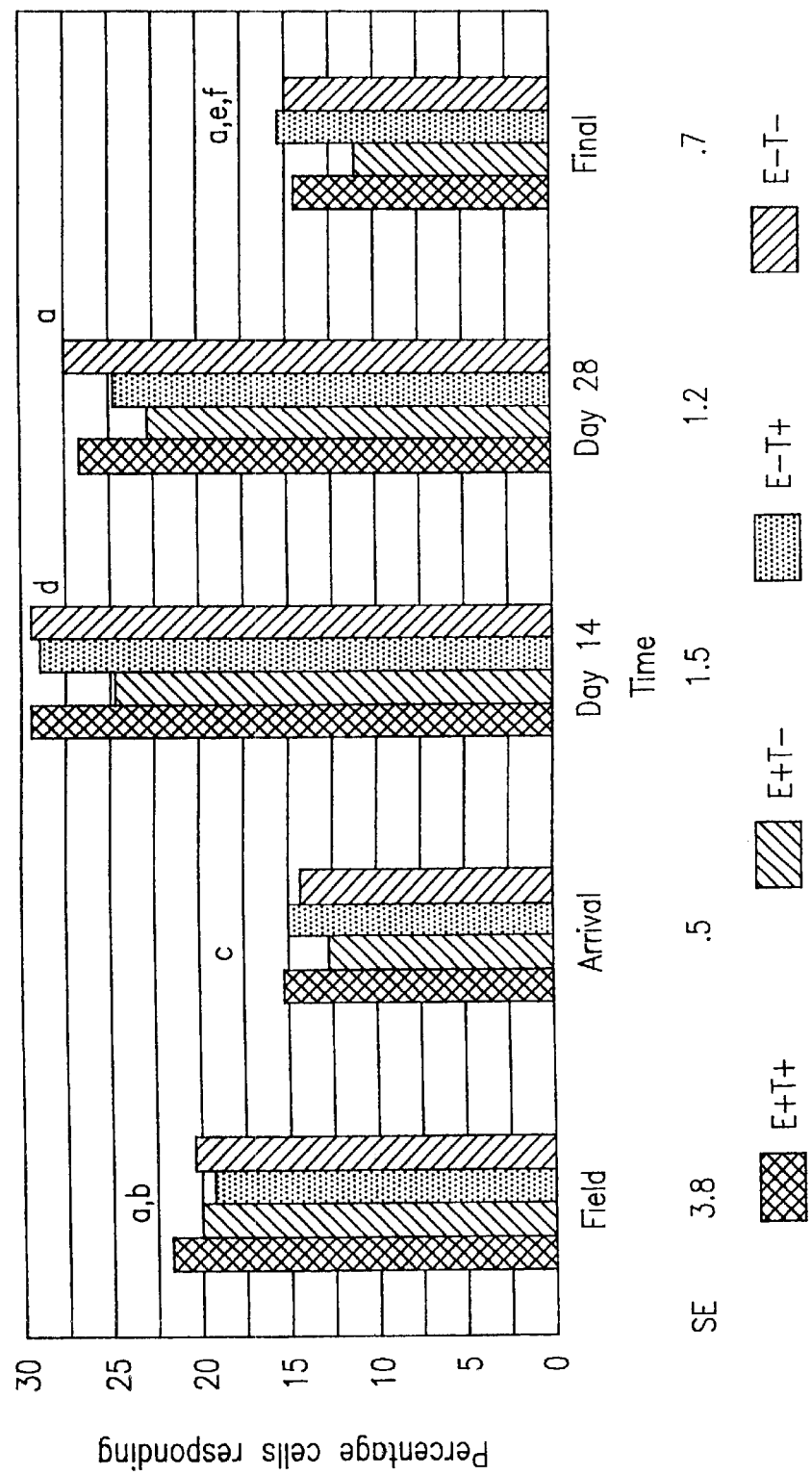
FIG. 4a is a graphic presentation of the effect of seaweed extract treatment of grass on phagocytic activity during the feedlot period of steers that had grazed the treated grass prior to the feedlot period and shows results of Example II.

In FIG. 4a, "a" indicates a Tasco™ by endophyte interaction (P<0.05), "b" indicates a location by Tasco™ by endophyte interaction (P<0.05) and "c" indicates a Tasco™ by endophyte interaction (P<0.10), "e" indicates a Tasco™ effect (<0.05) and "f" indicates an endophyte effect (P<0.01), and n=2 for each bar where pen is the experimental unit.

Figure 4B:
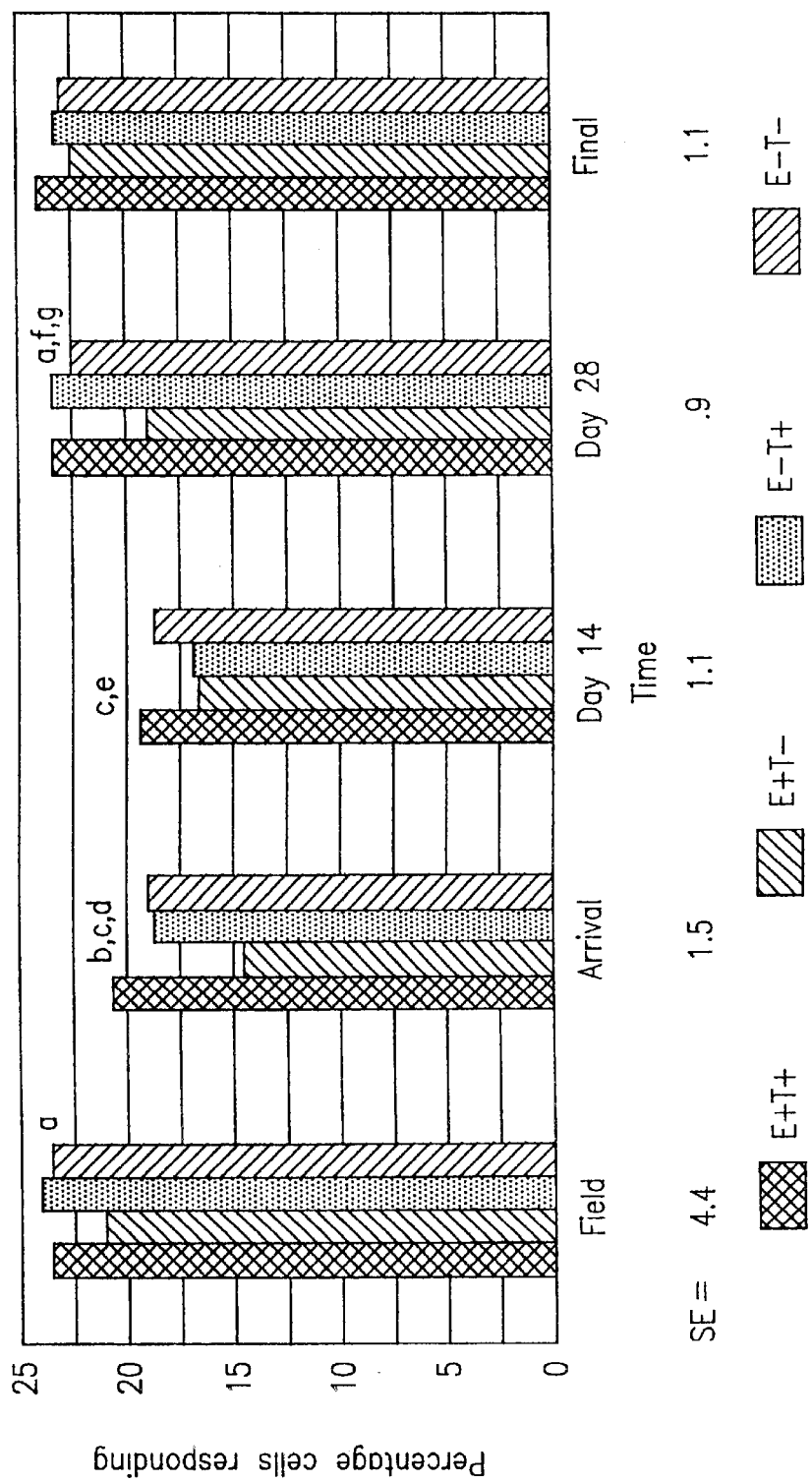
FIG. 4b is a graphic presentation of the effect of seaweed extract treatment of grass on monocyte major histocompatibility complex Class II expression during the feedlot period of steers that had grazed treated grass prior to the feedlot period and shows results of Example II.

In FIG. 4b, "a" indicates Tasco™ by endophyte interaction (P<0.05), "b" indicates a Tasco™ effect (P<0.08), "c" indicates a Tasco™ by endophyte interaction (P<0.07), "d" indicates a Tasco™ by copper interaction (P<0.07), "e" indicates a Tasco™ by copper interaction (P<0.05), "f" indicates a Tasco™ effect (P<0.02) and "g" indicates an endophyte effect (P<0.05), and n=12 for each bar where pen is the experimental unit.

Figure 5:
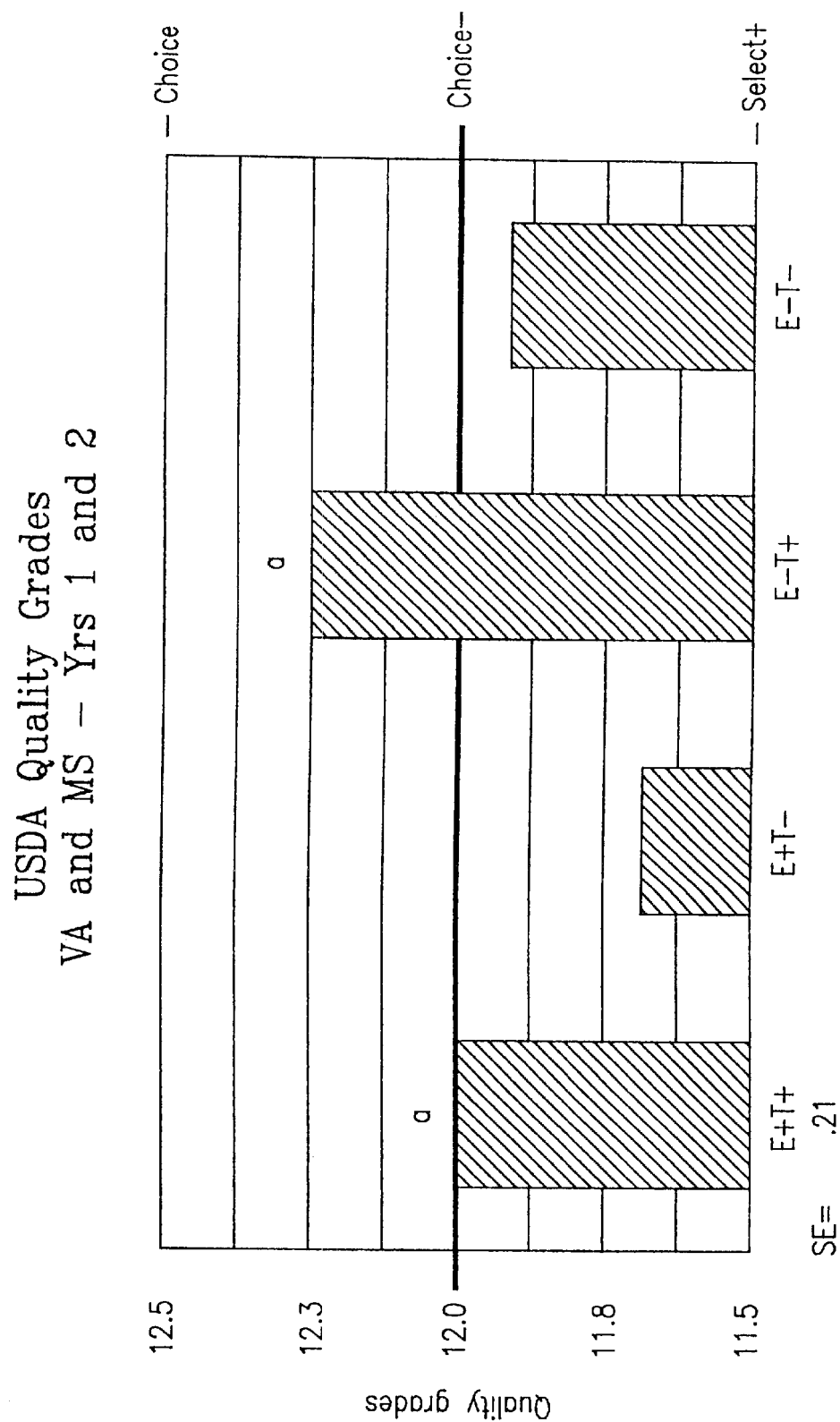
FIG. 5 is a graphic presentation of USDA Grades after feedlot phase resulting from seaweed extract treated grass grazed by steers and shows results of Example II.

In FIG. 5, "a" indicates a Tasco™ effect (P<0.15) and n=12 for each bar where pen is the experimental unit.

Figure 6:
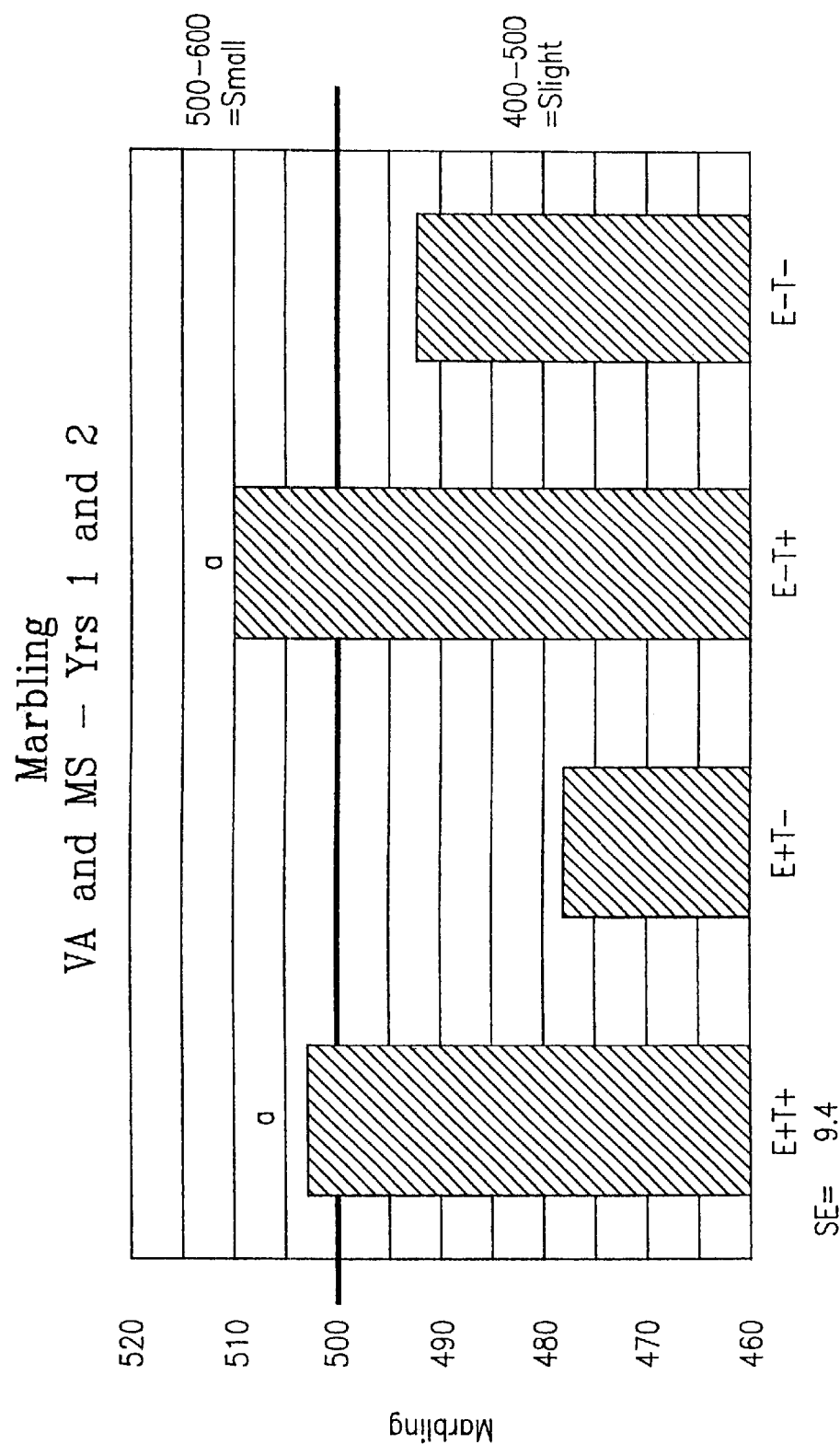
FIG. 6 is a graphic presentation of marbling score after feedlot phase resulting from seaweed extract treated grass grazed by steers and shows results of Example II.

In FIG. 6, "a" indicates a Tasco™ effect (P<0.05) and n=12 for each bar where pen is the experimental unit.

These trials showed that a positive immune response resulted from treatment of forage with seaweed and that it was not restricted to the endophyte infected fescue. These trials showed that the response was long term (132 days) after treatment ended and that there was an improvement in carcass value related to seaweed treatment.

EXAMPLE III

Two groups of steers (48 cattle in each group) were fed 0. 1.5, 3% by weight of their total daily dry matter intake as seaweed meal (Acadian Kelp Meal). Group one steers were fed a diet based on sorghum while group two was fed a diet based on corn. The trial was continued for 129 days at which time all steers were slaughtered.

Figure 7:
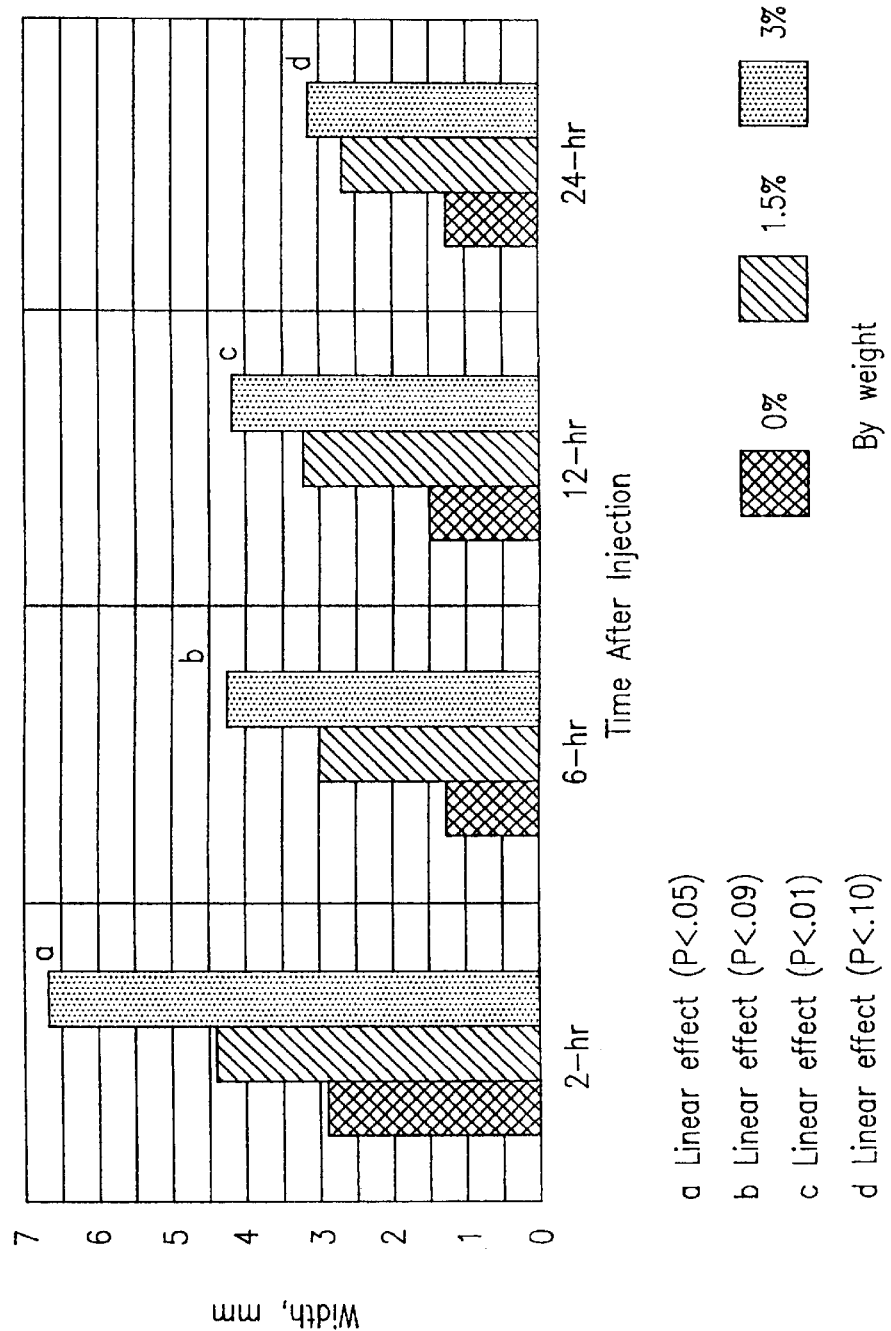
FIG. 7 is a graphic presentation of steers on seaweed meal-dry matter diet having increased immune function in regard to reaction to intradermal injections of phyto hemoaglutin, and shows results of Example III.

Inclusion of seaweed meal reduced daily dry matter intake and performance of steers. However, as shown in FIG. 7, there was increased immune function particularly in regard to reaction to intradermal injections of phyto hemoaglutin.

Inclusion of seaweed meal directly in the diet of beef cattle resulted in enhanced immune response in some indicators but was less effective than treating pastures with seaweed extract and allowing cattle to graze the treated forage.

EXAMPLE IV

Figure 8A:
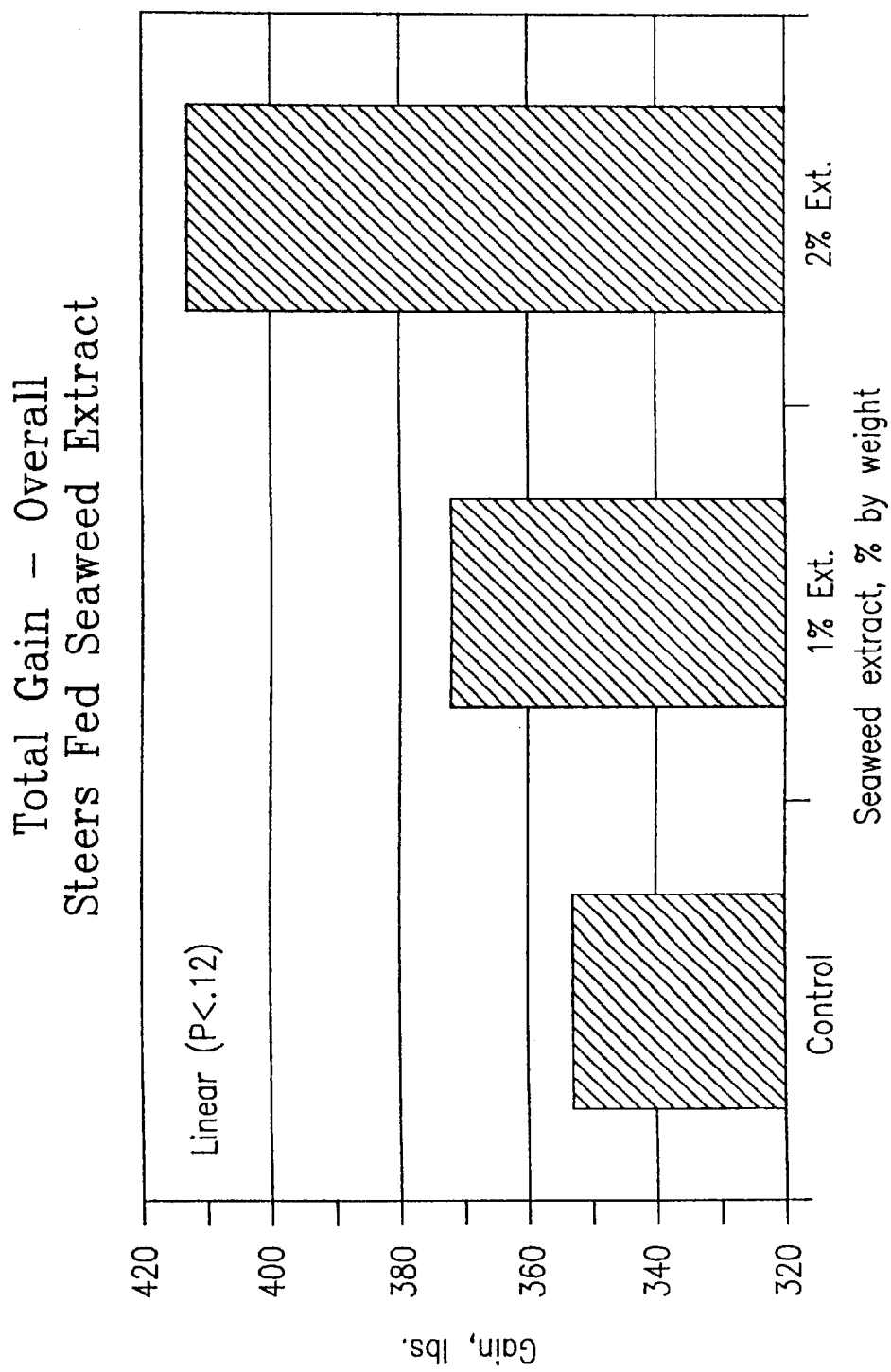
FIG. 8a is a graphic presentation of total gains of steers exposed to seaweed supplement during a 10 day feeding trial with seaweed extract (1 and 2%) and control, followed by feedlot finishing, and shows results of Example IV.
Figure 8B:
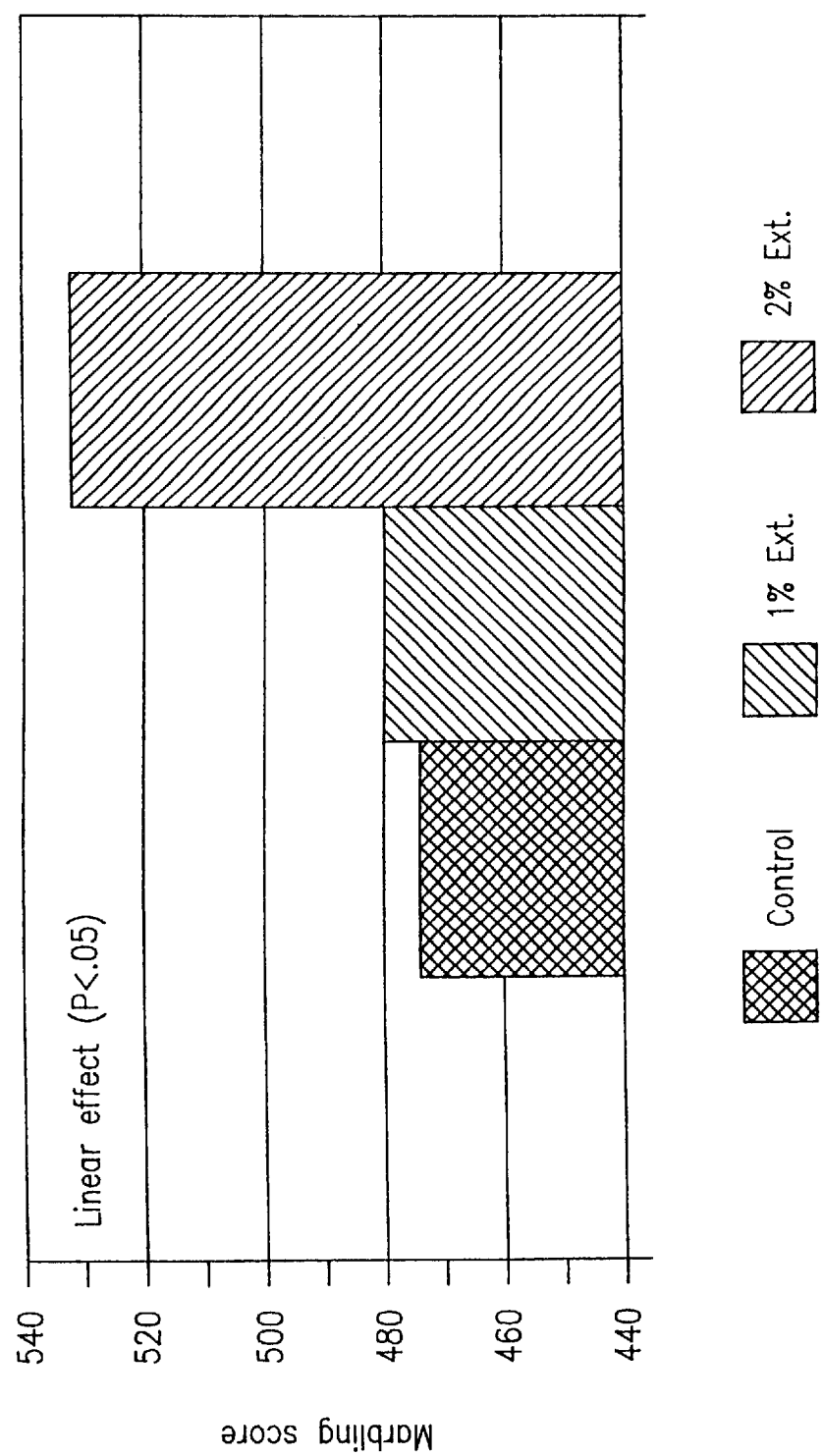
FIG. 8b is a graphic presentation of marbling in meat from slaughter of steers exposed to seaweed supplement during a 10 day feeding trial with seaweed extract (1 and 2%) and control, followed by feedlot finishing, and shows results of Example IV.
Figure 8C:
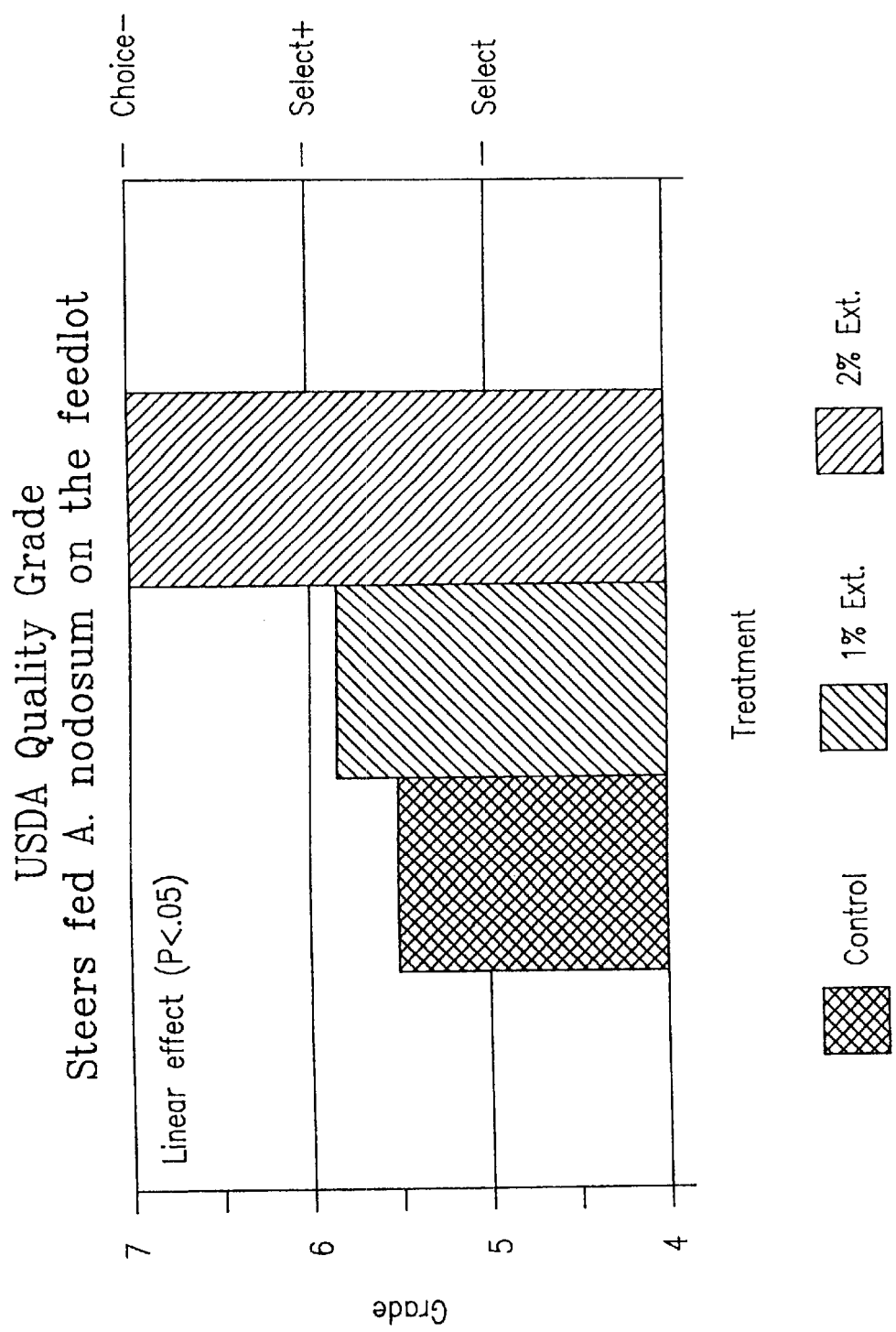
FIG. 8c is a graphic presentation of USDA Quality Grades for meat from slaughter of steers exposed to seaweed supplement during a 10 day feeding trial with seaweed extract (1 and 2%) and control, followed by feedlot finishing, and shows results of Example IV.

Twenty-four steers were fed a diet of 0, 1, and 2% seaweed extract (Acadian Soluble Seaweed Extract Powder) for 10 days in a feeding trial. At the end of the 10-day period, the extract was removed from the diet and all steers were fed the control diet. Daily gains were recorded. The results indicated a trend for a linear increase in total and daily gain in response to seaweed level (FIG. 8a). The improvement in performance appears to be consistent with research with pigs and lambs. At slaughter, there was a linear increase in marbling and in response to USDA Quality Grade in response to feeding seaweed extract. (FIGS. 8a and 8c). The improvement in marbling and grade appears to be consistent with results of research where seaweed extract was sprayed on tall fescue pastures grazed by steers.

EXAMPLE V

One hundred and twenty-eight baby pigs (males and females) were blocked by weight and breed and were randomized within blocks to four treatments as following: Control, 3% seaweed meal (Tasco-14™), 0.5% seaweed extract (Tasco-EX™), and 1% seaweed extract (Tasco-EX™) as a percentage by weight of the diet. Percentages were calculated as a percent of the diet on an as-fed basis. There were four pens (replications) per treatment with eight pigs per pen. Pigs were started on the experimental diets at weaning and were fed the diets during the entire 35-day nursery phase. Weights of pigs and feed intake were determined weekly. All pigs had been exposed to Porcine Respiratory and Reproductive Syndrome.

The diet aside from seaweed supplement was as follows: 64.2% ground milo, 32.5% soybean meal, 1.4% dicalcin phosphate, 1.1% calcium carbonate, 0.5% vitamin premix, 0.2% trace mineral premix and 0.1% magnesium oxide, the percentages being by weight. The seaweed supplement meal and the seaweed supplement extract (powder form) were admixed with diet by mixing in a mixer together with the other diet constituents.

Figure 10:
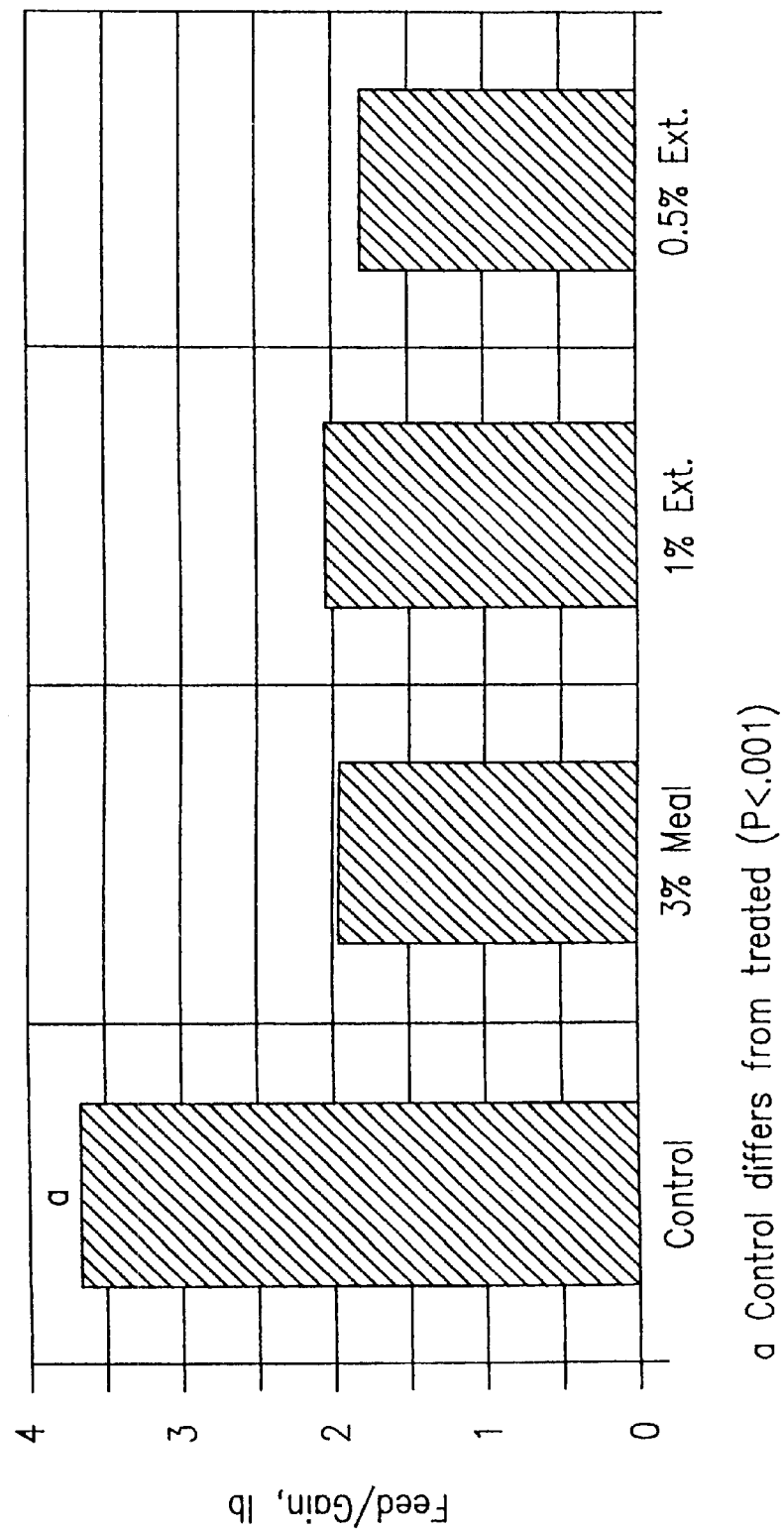
FIG. 10 is a graphic presentation of baby pig trial feed to gain for control, 3% seaweed meal, 1% seaweed extract, and 0.5% seaweed extract, showing results of Example V.
Figure 11:
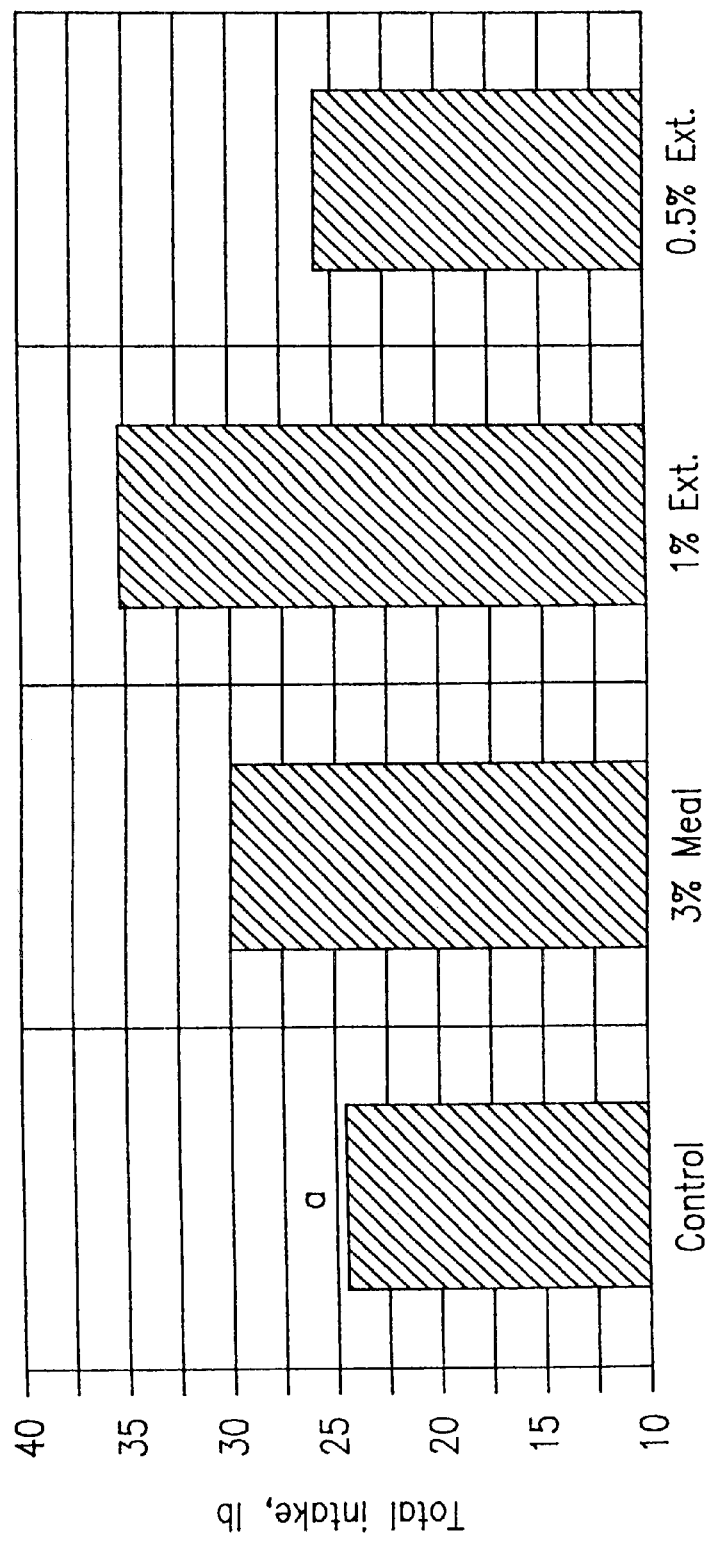
FIG. 11 is a graphic presentation of baby pig trial total intake per pig for control, 3% seaweed meal, 1% seaweed extract, and 0.5% seaweed extract, showing results of Example V.
Figure 12:
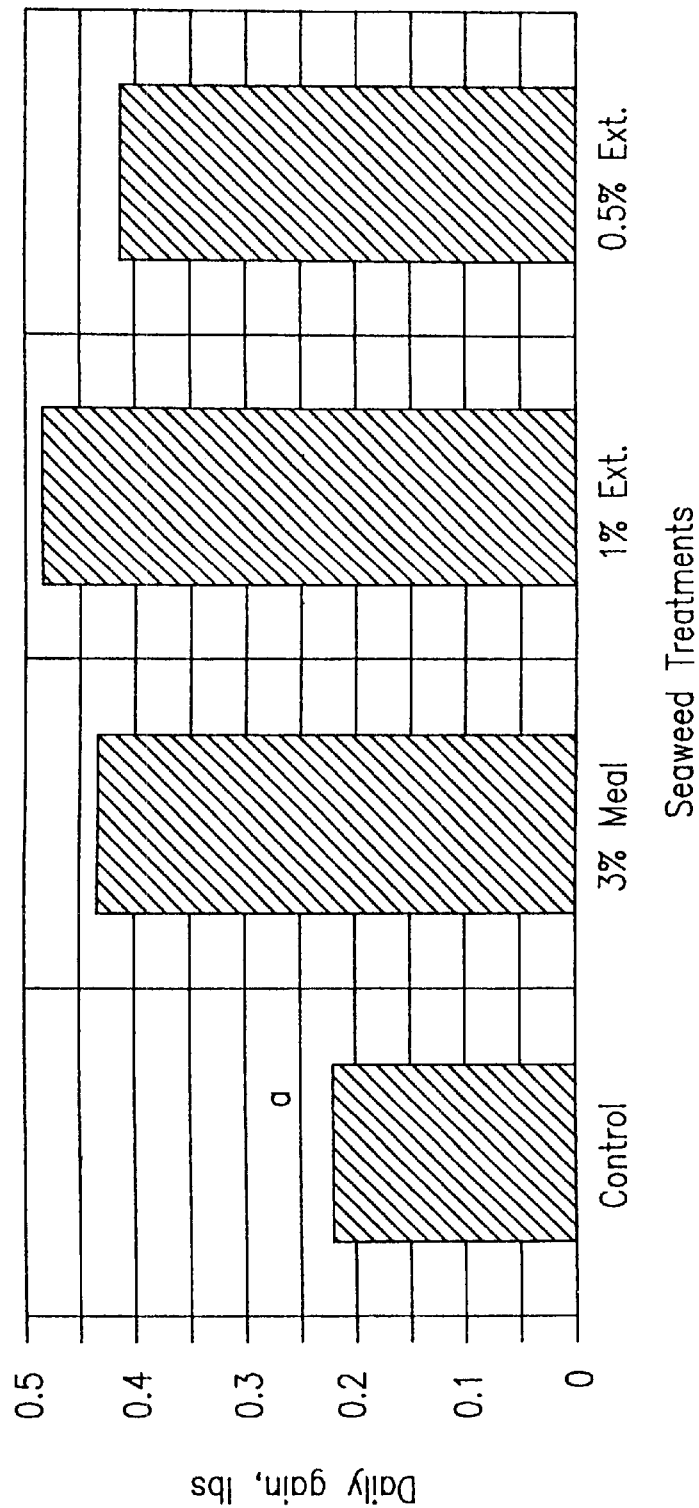
FIG. 12 is a graphic presentation of baby pig trial daily gains for control, 3% seaweed meal, 1% seaweed extract, and 0.5% seaweed extract, showing results of Example V.
Figure 13:
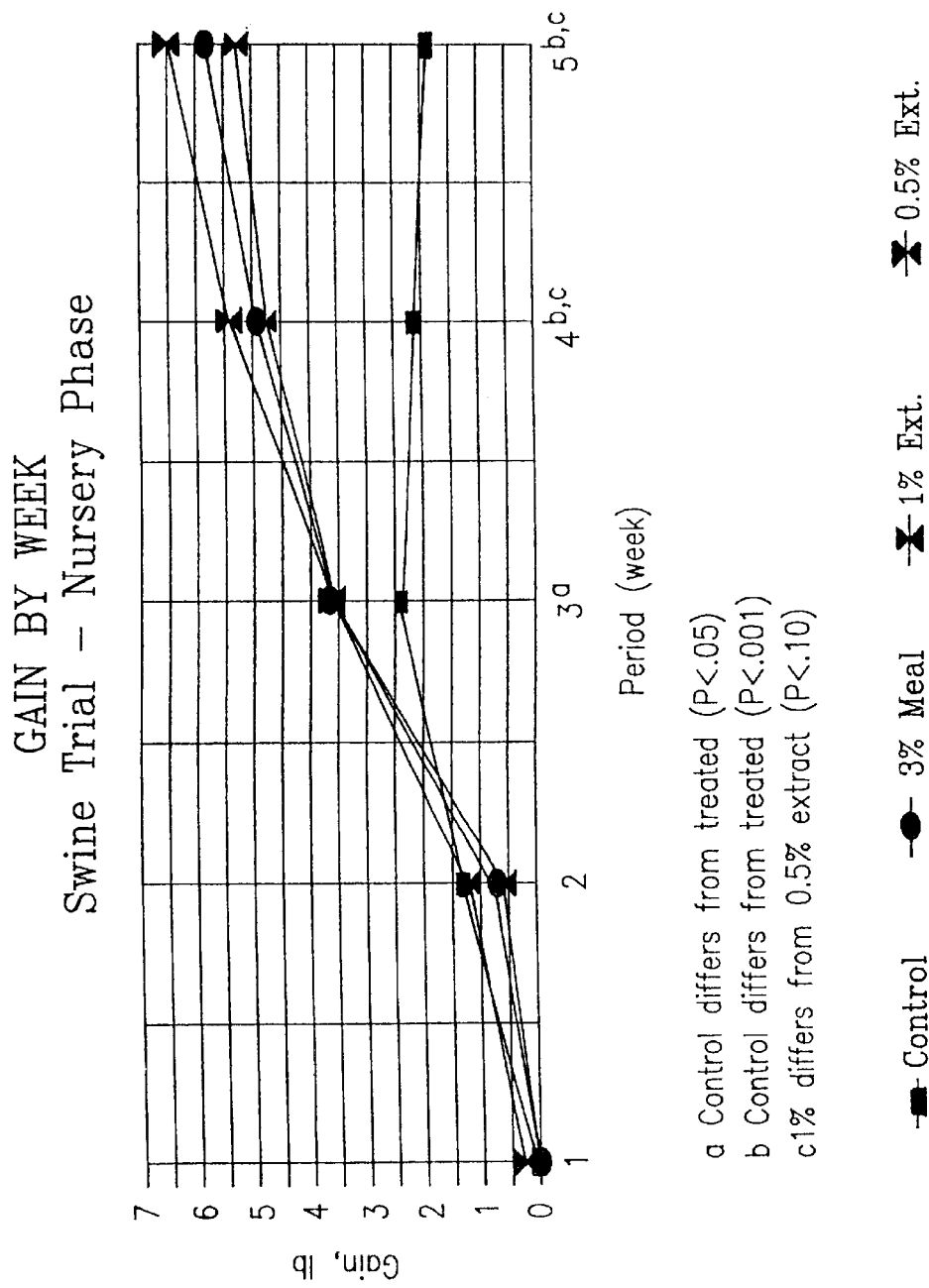
FIG. 13 is a graphic presentation of baby pig trial gains by week for control, 3% seaweed meal, 1% seaweed extract, and 0.5% seaweed extract, showing results of Example V.
Figure 14:
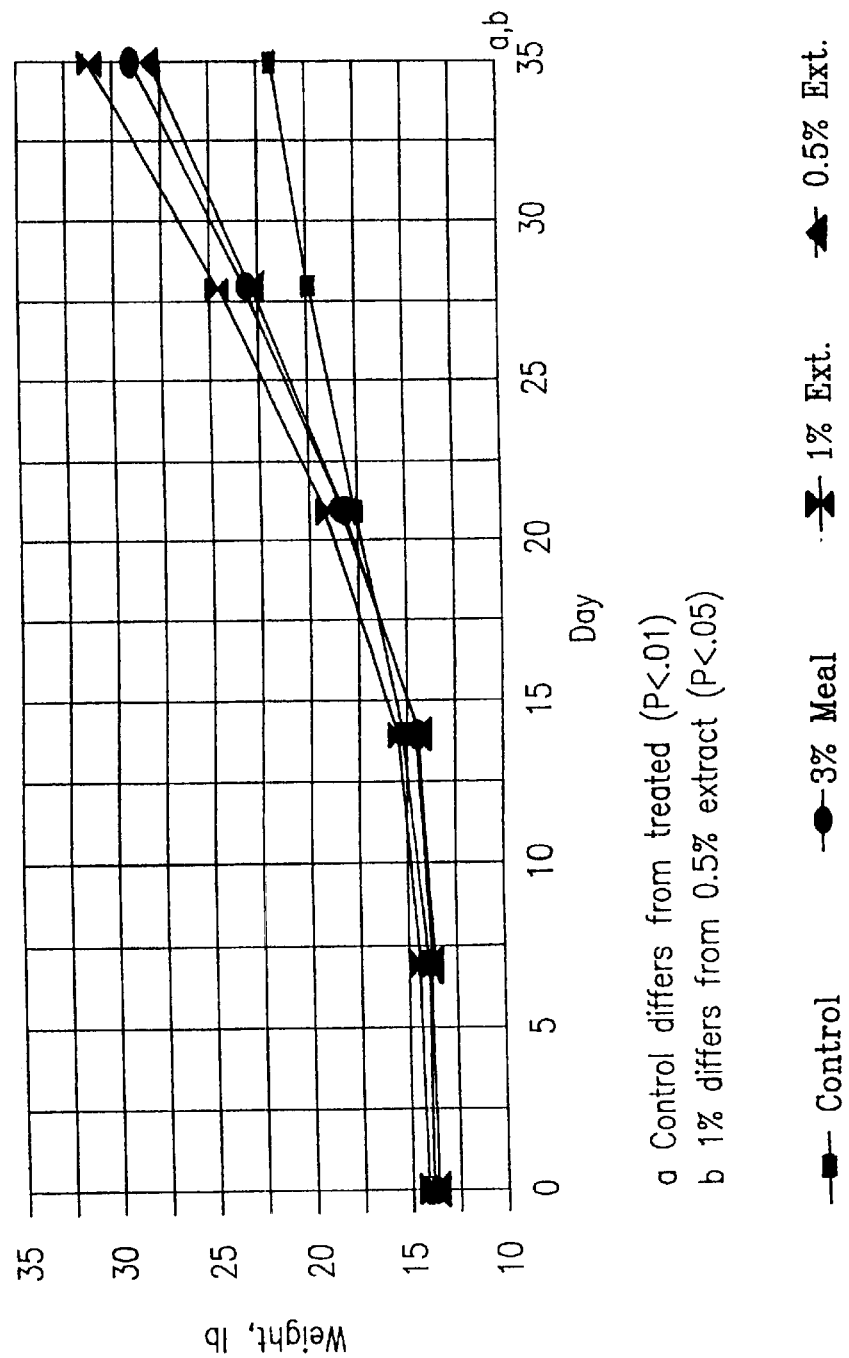
FIG. 14 is a graphic presentation of baby pig trial body weights through day 35 for control, 3% seaweed meal, 1% seaweed extract, and 0.5% seaweed extract, showing results of Example V.
Figure 15:
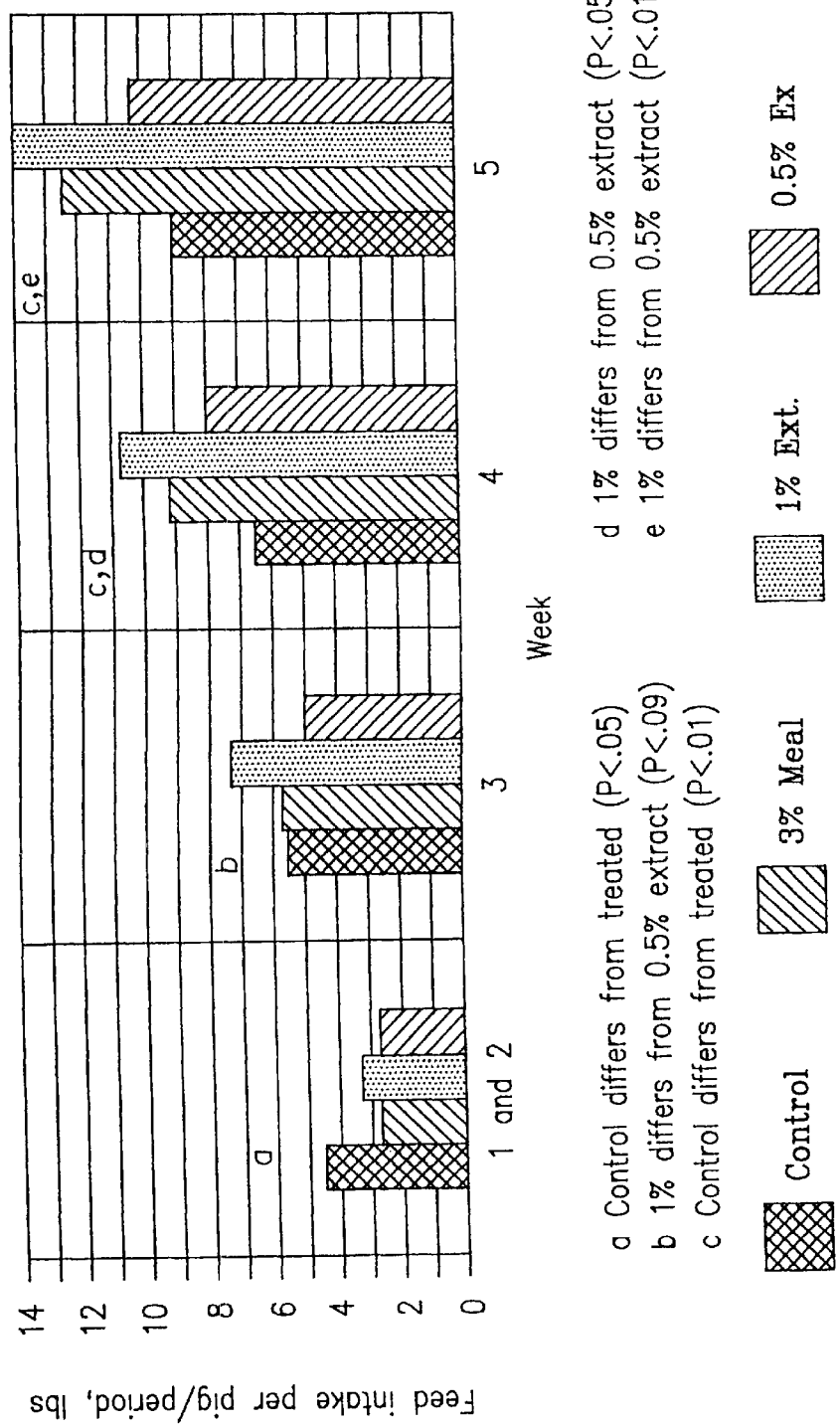
FIG. 15 is a graphic presentation of baby pig trial feed intake per pig per period for control, 3% seaweed meal, 1% seaweed extract and 0.5% seaweed extract, showing results of Example V.

Results are shown in FIGS. 9–15 where "Ext." means seaweed extract. As shown in FIG. 12, the diets with seaweed supplement gave higher daily gains. As shown in FIG. 13, the diets with seaweed supplement gave higher weekly gains starting in week 3 of the nursery phase. As shown in FIG. 9, the diets with seaweed supplement gave higher total gain. As shown in FIG. 14, the diets with seaweed supplement gave higher body weights starting at day 30 of the nursery phase. As shown in FIG. 11, the diets with seaweed supplement gave higher total intake per pig; FIG. 15 shows the intake per pig in the period of weeks 1 and 2, in the period of week 3, in the period of week 4 and in the period of week 5. As shown in FIG. 10, the diets with seaweed supplement gave lower feed to gain ratios.

Performance of control pigs declined over the feeding period while performance of treated pigs improved.

The results indicate that direct feeding of seaweed supplement improved the ability of disease-stressed baby pigs (by exposure to PRRS disease) to overcome the disease challenge and improve in performance.

EXAMPLE VII

In this study, 10 mares and their foals were fed seaweed extract (Tasco™-Ex) in amount of 2% of the total diet and 10 were fed a normal diet, for 14 days prior to weaning.

The diet aside from seaweed supplement was as follows: 46% oats, 37% corn, 5.5% soybean meal, 5.4% molasses, 4% fat, 1.1% dicalcium phosphate, 0.7% calcium carbonate and 0.3% vitamin/mineral premix.

The seaweed extract powder was admixed with diet to provide diet for the mares fed seaweed supplemented diet by hand mixing into the diet at the time of feeding. Each mare was individually fed.

Blood samples were collected at the start of the study, at weaning, and three times more to determine the effect of weaning and handling on the neutrophil to lymphocyte ratio aspect of the immune system.

Figure 16:
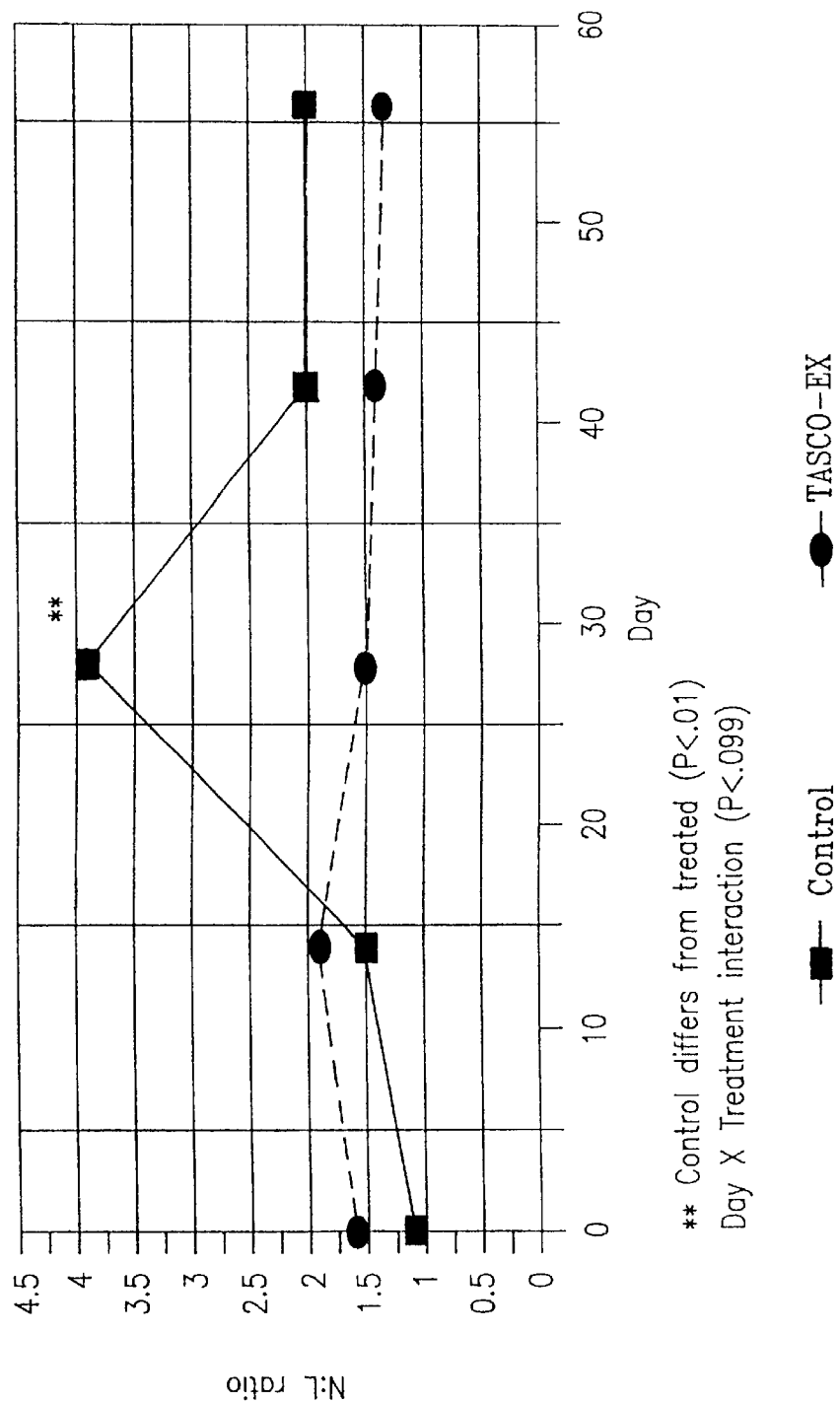
FIG. 16 is a graphic presentation of neutrophil to lymphocyte ratio for lactating mares for 56 days after weaning for control diet and seaweed extract at 2% of total diet and shows results of Example VI.

The results are shown in FIG. 16.

Normally, horses have about 54% neutrophils and 35% lymphocytes which is a ratio of neutrophils to lymphocytes of about 1.5:1. As indicated in FIG. 16, control mares (not fed seaweed supplement) had elevated neutropbil to lymphocyte ratio increasing to near 4.0 on day 28. As shown in FIG. 16, for mares fed diet with seaweed supplement, the neutrophil to lymphocyte ratio was consistent at around 1.5.

These findings indicate that feeding seaweed supplement to lactating mares prior to weaning mitigated the stress of weaning and handling, especially on day 28.

Similar results of mitigating the stress of weaning and handling are obtained, when the lactating mares are grazed on seaweed extract treated pasture or seaweed meal treated pasture instead of being directly feed seaweed extract and diet as described above.

For purposes of this specification and figures, the following abbreviations are defined as follows:

| | |
|---|---|
| S.E. | standard error; |
| E+ | endophyte infected; |
| E− | no endophyte infection; |
| T+ | with seaweed; and |
| T− | without seaweed. |

The terms and expressions which have been employed are used as terms of description and not of limitation, and it is not intended in the use of such terms and expressions to exclude an equivalence of the features shown and described or portions thereof since it is recognized that various modifications are possible within the scope of the invention claimed.

What is claimed is:

1. A method of imparting resistance to porcine reproductive and respiratory syndrome disease, denoted PRRS disease in pigs that have been exposed to PRRS disease, comprising administering a PRRS disease resistance imparting effective amount ranging from 0.1 to 5% by weight of diet of seaweed supplement from *Ascophyllum nodosum* to pigs that have been exposed PRRS disease.

2. The method of claim 1 wherein the amount administered ranges from 0.2 to 5% by weight of diet.

3. The method of claim 1 wherein the pigs are baby pigs entering or in the nursery phase.

4. The method of claim 1 wherein the administering comprises feeding the pigs seaweed supplement during the entire nursery phase.

5. The method of claim 1 where the administering is carried out by directly feeding seaweed supplement in admixture with diet.

6. The method of claim 1 wherein the seaweed supplement is seaweed extract.

7. The method of claim 1 wherein the seaweed supplement is seaweed meal.

8. A method of imparting resistance to porcine reproductive and respiratory syndrome disease, denoted PRRS disease, in pigs that have been exposed to PRRS disease, comprising administering a PRRS disease resistance imparting effective amount ranging from 0.5 to 5% by weight of diet of seaweed supplement from *Ascophyllum nodosum* to pigs that have been exposed to PRRS disease.

* * * * *